(12) United States Patent
Little et al.

(10) Patent No.: US 10,736,674 B2
(45) Date of Patent: Aug. 11, 2020

(54) INTRAMEDULLARY DEVICE

(71) Applicant: The Sydney Children's Hospitals Network (Randwick and Westmead), Westmead, New South Wales (AU)

(72) Inventors: David Little, Surry Hills (AU); Justin Bobyn, West Pennant Hills (AU)

(73) Assignee: SYDNEY CHILDREN'S HOSPITALS NETWORK (RANDWICK AND WESTMEAD), New South Wales (AU)

( * ) Notice: Subject to any disclaimer, the term of this patent is extended or adjusted under 35 U.S.C. 154(b) by 106 days.

(21) Appl. No.: 15/111,135

(22) PCT Filed: Jan. 15, 2015

(86) PCT No.: PCT/AU2015/050014
§ 371 (c)(1),
(2) Date: Jul. 12, 2016

(87) PCT Pub. No.: WO2015/106319
PCT Pub. Date: Jul. 23, 2015

(65) Prior Publication Data
US 2016/0331421 A1    Nov. 17, 2016

(30) Foreign Application Priority Data

Jan. 17, 2014  (AU) ............................ 2014900144
May 9, 2014   (AU) ............................ 2014901732

(51) Int. Cl.
A61B 17/72   (2006.01)
A61B 17/70   (2006.01)
A61B 17/86   (2006.01)

(52) U.S. Cl.
CPC ...... *A61B 17/7241* (2013.01); *A61B 17/7002* (2013.01); *A61B 17/7004* (2013.01);
(Continued)

(58) Field of Classification Search
CPC ............ A61B 17/7283; A61B 17/7216; A61B 17/7225; A61B 17/72; A61B 17/7025
See application file for complete search history.

(56) References Cited

U.S. PATENT DOCUMENTS 4,467,794 A * 8/1984 Maffei .................. A61B 17/72
                                                        403/47
4,854,312 A * 8/1989 Raftopoulos ...... A61B 17/7266
                                                        606/68

(Continued)

OTHER PUBLICATIONS

EP Appln. 15737563.5, prosecution documents submitted in response to official communication dated Sep. 22, 2017, 32 pages Mar. 8, 2018.

(Continued)

*Primary Examiner* — Julianna N Harvey
(74) *Attorney, Agent, or Firm* — John V. Daniluck; Dentons Bingham Greenebaum LLP

(57) ABSTRACT

An intramedullary orthopaedic device is disclosed including an intramedullary rod configured for insertion into a bone, the rod including a first elongate member having a first mating surface and at least a second elongate member having a second mating surface. The first mating surface is configured to engage with the second mating surface such that the elongate members are longitudinally moveable but substantially not rotationally moveable relative to each other. Each mating surface can have an elongate ridge and an elongate groove. A guided growth system and method is also disclosed.

52 Claims, 24 Drawing Sheets

(52) U.S. Cl.
CPC ...... *A61B 17/7014* (2013.01); *A61B 17/7283* (2013.01); *A61B 17/863* (2013.01); *A61B 17/8625* (2013.01); *A61B 17/8685* (2013.01)

(56) References Cited

U.S. PATENT DOCUMENTS

| | | | |
|---|---|---|---|
| 5,074,882 | A | 12/1991 | Grammont et al. |
| 5,516,335 | A | 5/1996 | Kummer et al. |
| 5,976,137 | A * | 11/1999 | Mayer ............... A61B 17/1659 606/300 |
| 6,755,862 | B2 | 6/2004 | Keynan |
| 8,034,054 | B2 * | 10/2011 | Griggs ............... A61B 17/7216 606/63 |
| 8,128,627 | B2 * | 3/2012 | Justin ............... A61B 5/107 606/60 |
| 2010/0137913 | A1 | 6/2010 | Khatchadourian et al. |
| 2012/0203278 | A1 | 8/2012 | Gil et al. |
| 2012/0209267 | A1 * | 8/2012 | Lee ............... A61B 17/7283 606/62 |

OTHER PUBLICATIONS

EP Search Report, Serial No. 157375635, 10 pages Sep. 6, 2017.
AU Patent Office, Serial No. PCT/AU2015/050014, Written Opinion, 7 pages Feb. 16, 2015.
AU Patent Office, Serial No. PCT/AU2015/050014, International Search Report Feb. 16, 2015.
WIPO, International Preliminary Report on Patentability, PCT/AU2015/050014, 6 pages Jul. 19, 2016.
JP Office Action, Appln. No. 2016-546965, JPO, 7 pgs. Nov. 6, 2018.
AU Appln 2015207673, Examination Report No. 2, 4 pgs. Aug. 8, 2019.
JP Appln. 2016-546965, Resposne to JP Office Action, 9 pgs. Apr. 1, 2019.
AU Appln. 2015207673, Response to Office Action, 26 pgs. Jul. 15, 2019.

* cited by examiner

Figure 18a
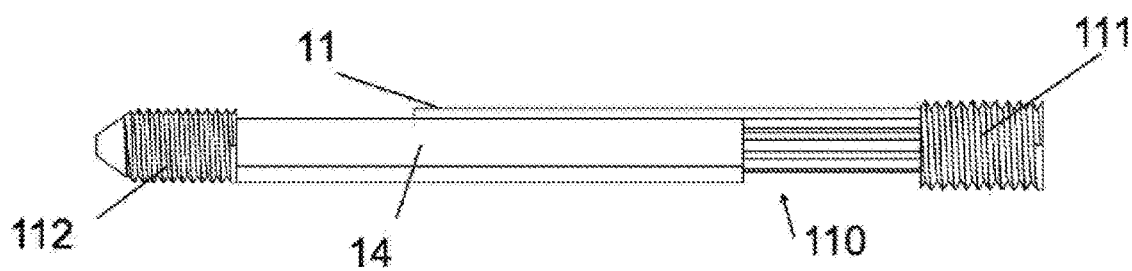
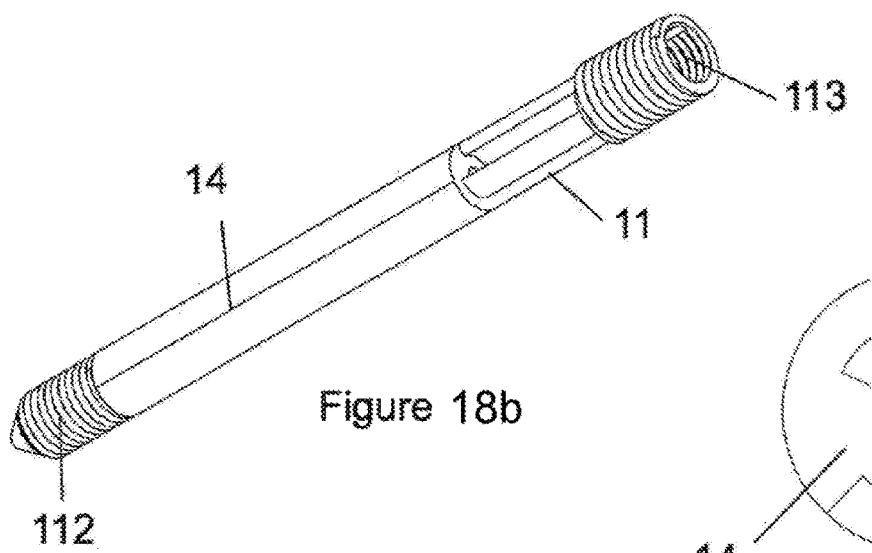
Figure 18b
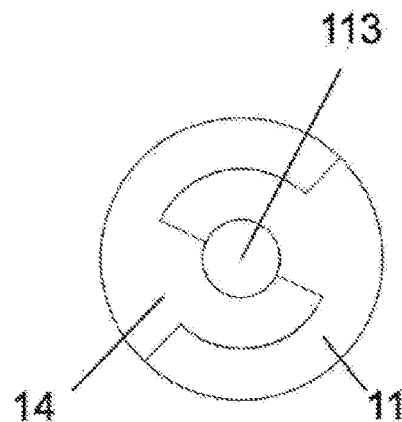
Figure 18d
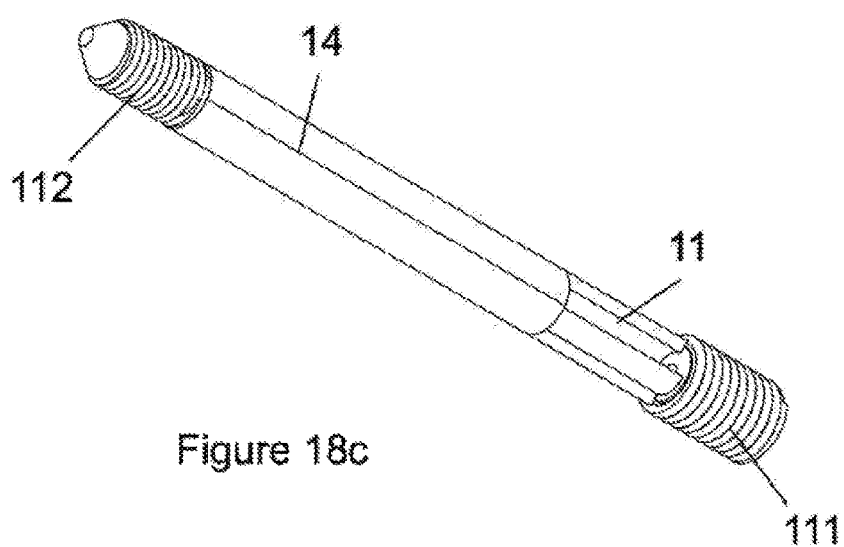
Figure 18c

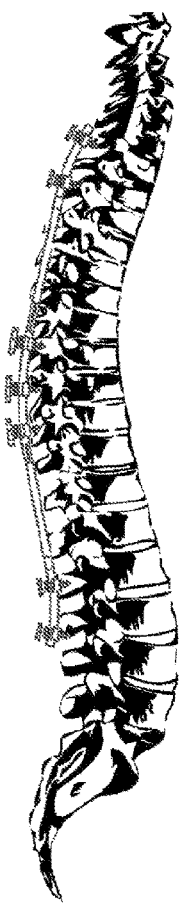
Figure 25a
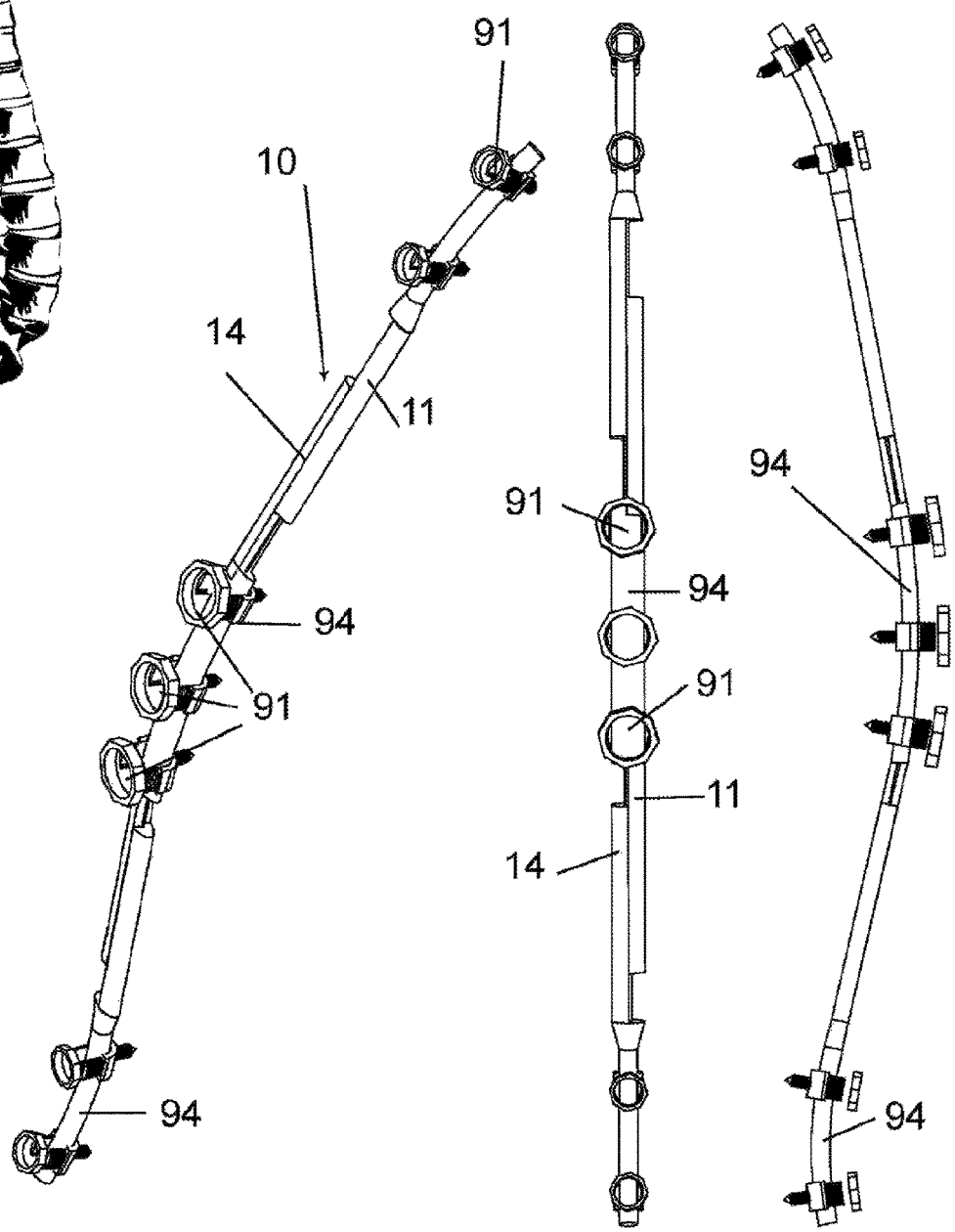
Figure 25 b
Figure 25 c
Figure 25 d

Fibure 26b

INTRAMEDULLARY DEVICE

CROSS-REFERENCE TO RELATED APPLICATIONS

The present application is a U.S. National Phase Application of PCT International Application Number PCT/AU2015/050014, filed on 15 Jan. 2015, designating the United States of America and published in the English language, which is an International Application of and claims priority from Australian Provisional Patent Application No 2014900144 filed on 17 Jan. 2014 and Australian Provisional Patent Application No 2014901732 filed on 9 May 2014, the contents of which are incorporated herein by reference.

FIELD OF THE DISCLOSURE

The disclosure relates to an orthopaedic device, system and method for providing stabilisation of a bone and being configured to allow extension of the device with the growth or movement of the bone.

BACKGROUND

Orthopedic surgery utilises many devices such as rods, nails, plates and screws to hold bone together post fracture or fusion or provide stabilisation such as in spinal stabilisation procedures. In children, growth presents a major problem and has historically required multiple surgeries. While rods which have the capacity to lengthen as the patient grows have subsequently been developed, they are not without their problems, in large caused by the fact that they typically rely on a two component system with one rod telescoping into the interior of another rod.

Complications and problems arise in part due to the fact that in a telescoping arrangement, one of the rods must necessarily have a smaller diameter than the other rod. Thus no matter what the material, the moment of inertia of the lesser diametered part of the system is less and can lead to part of the rod bending as the child grows or acutely deforming in a fracture event. Further, while the smaller rod may be cross-locked in some instances with a small K wire, this is a difficult procedure and the resulting rod/wire structure is often not durable.

Further, as the telescopic rods are circular, they do not confer appropriate rotational stability to the system and complications can result from a negative telescoping of the rods.

Another instance of the use of extensible orthopaedic devices is in young patients with spinal deformity. Recent clinical management trends have been to place corrective fixation rods without fusing the spine. These rods can then be adjusted (lengthened) as the child grows to improve final height at the time of definitive fusion.

Growing rod spinal techniques include distraction-based systems and guided growth systems. Although several devices are known, there is a need to provide a stable device which allows for "guided growth" both using the natural growth of the bone being the "motor" for extending the device and using non-natural mechanisms to distract the bone.

In addition to stabilisation and growth of the long bones and the spine, other procedures also call for the use of a device which extends with the bone. In all such cases, it would be desirable to provide a device which is stable and which extends either through the natural growth of the bone or is suitable for use with other "motors" for growth to achieve lengthening of a bone.

Any discussion of documents, acts, materials, devices, articles or the like which has been included in the present specification is not to be taken as an admission that any or all of these matters form pert of the prior art base or were common general knowledge in the field relevant to the present disclosure as it existed before the priority date of each claim of this application.

SUMMARY

In one aspect, there is provided an intramedullary orthopaedic device comprising:
an intramedullary rod configured for insertion into a bone; said intramedullary rod including:
  a first elongate member having a first mating surface; and
  at least a second elongate member having a second mating surface;
  wherein, the first mating surface is configured to engage with the second mating surface such that the elongate members are longitudinally moveable but substantially not rotationally moveable relative to each other.

The first mating surface may comprise a first elongate ridge and a first elongate groove. The first elongate ridge may extend from a base of the mating surface and may have a variable diameter along its extension. Typically, the first elongate ridge comprises a relatively narrow neck extending into a relatively wider protrusion.

At least part of the first elongate groove may be defined by at least part of the first elongate ridge. In this embodiment, at least part of the first elongate ridge defines part of an opening of the first elongate groove.

The first elongate groove may have a wider base relative to the opening.

In another embodiment, the first elongate groove may have a shape that is the inverse of the shape of the first elongate ridge.

Further, the second mating surface may comprise a second elongate ridge and a second elongate groove. The second elongate ridge typically extends from a base of the second mating surface and has a variable diameter along its extension. In one embodiment, the second elongate ridge comprises a relatively narrow neck extending into a relatively wider protrusion.

At least part of the second elongate groove may be defined by at least part of the second elongate ridge. In one embodiment, at least part of the second elongate ridge defines part of an opening of the second elongate groove.

The second elongate groove may have a wider base relative to the opening. Further, the second elongate groove may have a shape that is the inverse of the shape of the second elongate ridge.

The first mating surface may be a mirror image of the second mating surface.

The first elongate groove may be the inverse of the shape of the second elongate ridge. Further, the second elongate groove may be the inverse of the shape of the first elongate ridge.

The first elongate member typically further comprises a first non-mating surface and the second elongate member comprises a second non-mating surface. The first non-mating surface may be substantially identical to the second non-mating surface.

When the first mating surface is in engagement with the second mating surface, the first non-mating surface and the second non-mating surface may together define an outer surface of the intramedullary orthopaedic device. The outer surface may be substantially circular in cross section.

In another aspect, there is provided a guided growth system comprising: an intramedullary rod configured for insertion into a bone; said intramedullary rod including:

a first elongate member having a first mating surface extending from a first bone fixation region; and at least a second elongate member having a second mating surface extending from a second bone fixation region;

the first mating surface engageable with the second mating surface such that the elongate members are longitudinally moveable but substantially not rotationally moveable relative to each other; and wherein when the first and second bone fixation regions are attached to surrounding bone, growth of the bone causes the elongate members to move longitudinally relative to one another.

The intramedullary rod typically has a first implantable configuration wherein a substantial length of the first mating surface engages an equal length of the second mating surface. In the implantable configuration said substantial length of the first mating surface may comprise the entire length of the first mating surface. Alternatively, said substantial length may comprise 90%, 80%, 70%, 60%, 50%, 40%, or 30% of the length of the first mating surface.

In another aspect, there is provided a method of guiding growth of a bone of a subject including:

providing a first elongate member having a first mating surface extending from a first bone fixation region; and at least a second elongate member having a second mating surface extending from a second bone fixation region; the first mating surface engageable with the second mating surface such that the first and second elongate members are longitudinally moveable but substantially not rotationally moveable relative to each other;

assembling the first and second elongate members together into a first insertion assembly wherein a substantial length of the first mating surface is in engagement with a corresponding length of the second mating surface, the insertion assembly having a length n;

inserting the insertion assembly into the bone and advancing a distal end of the insertion assembly to a desired distal location within the bone;

securing the first bone fixation region of the first elongate member to surrounding bone at said distal location;

securing the second bone fixation region of the second elongate member to surrounding bone at a desired proximal location within the bone;

such that as the bone grows, the first and the second elongate members move longitudinally relative to each other to allow the insertion assembly to lengthen to a length greater than n as the bone grows.

In another aspect, there is provided:

an intramedullary orthopaedic device comprising;

an intramedullary rod configured for insertion into a bone; said intramedullary rod including:

a first elongate member extending from a first end to a second end; and at least a second elongate member also extending from a first end to a second end;

each elongate member including a bone fixation region and a mating region which is configured for engagement with the mating region of the other elongate member, wherein said first and at least second elongate member are longitudinally moveable relative to the other, and wherein;

the mating region of the first elongate member has a profile which is a mirror image of a profile of the mating region of the second elongate member.

In a further aspect, there is provided an intramedullary orthopaedic device comprising:

an intramedullary rod configured for insertion into a bone; said intramedullary rod including:

a first elongate member extending from a first end to a second end; and at least a second elongate member also extending from a first end to a second end;

each elongate member including a bone fixation region and a mating region which is configured for engagement with the mating region of the other elongate member;

wherein said first and at least second elongate members are longitudinally moveable relative to each other, and further wherein said engagement of at least part of the respective mating regions forms a mating interlock zone, and wherein when said first and at least second elongate members are matingly interlocked, the elongate members are longitudinally moveable but substantially not rotationally moveable relative to each other.

In this aspect, the configuration of the mating region substantially prevents said rotational movement of the elongate members relative to each other. Further, the two elongate members may be substantially non-telescopically arranged relative to one another.

In a further aspect, there is provided an intramedullary orthopaedic device comprising:

an intramedullary rod configured for insertion into a bone; said intramedullary rod including:

a first elongate member extending from a first end to a second end; and at least a second elongate member also extending from a first end to a second end;

each elongate member including a bone fixation region and a mating region which is configured for engagement with the mating region of the other elongate member, wherein said first and at least second elongate member are longitudinally moveable relative to the other, and further wherein said engagement of at least part of the respective mating regions forms a mating interlock zone which allows longitudinal movement of the elongate members relative to each other but substantially prevents rotational movement of either elongate member relative to the other and wherein said elongate members are substantially non-telescopically arranged relative to one another.

An orthopaedic device for attachment to a bone of a subject, said device comprising:

a first elongate member extending from a first end to a second end; and at least a second elongate member also extending from a first end to a second end;

each elongate member including a bone fixation region and a mating region configured for engagement with the mating region of the other elongate member, wherein said first and at least second elongate member are longitudinally moveable relative to the other, and further wherein;

a profile of the mating region of the first elongate member is the mirror image of a profile of the mating region of the second elongate member.

An orthopaedic device for attachment to a bone of a subject, said device comprising:

a first elongate member extending from a first end to a second end; and at least a second elongate member also extending from a first end to a second end;

each elongate member including a bone fixation region and a mating region which is configured for engagement with the mating region of the other elongate member, wherein said first and at least second elongate member are longitudinally moveable relative to the other, and further wherein said engagement of at least part of the respective mating regions forms a mating interlock zone to substantially prevent rotational movement of either elongate member relative to the other while allowing longitudinal movement of the elongate members relative to each other.

In this aspect, again, it is the configuration of the mating region which substantially prevents said rotational movement of the elongate members relative to each other. Further, the two elongate members may be substantially non-telescopically arranged relative to one another.

An orthopaedic device for attachment to a bone of a subject, said device comprising:

a first elongate member extending from a first end to a second end; and at least a second elongate member also extending from a first end to a second end;

each elongate member including a bone fixation region and a mating region which is configured for engagement with the mating region of the other elongate member, wherein said first and at least second elongate member are longitudinally moveable relative to the other, and further wherein said engagement of at least part of the respective mating regions forms a mating interlock zone which allows longitudinal movement of the elongate members relative to each other but substantially prevents rotational movement of either elongate member relative to the other and wherein said elongate members are substantially non-telescopically arranged relative to one another.

In another aspect, there is an orthopaedic device for attachment to a bone of a subject, said device dissected axially into:

a first elongate member extending from a first end to a second end; and at least a second elongate member also extending from a first end to a second end;

each elongate member including a bone fixation region and a mating region, said mating region configured for interdigitating engagement with the mating region of the other elongate member;

wherein said first and at least second elongate members are longitudinally moveable relative to each other.

In a further aspect, there is provided an orthopaedic device for attachment to a bone of a subject, said device comprising:

a first elongate member extending from a first end to a second end; and at least a second elongate member also extending from a first end to a second end;

each elongate member including a bone fixation region and a mating region for engagement with a mating region of the other elongate member, said mating regions of both the first and at least second elongate members including a male and a female component, wherein when the first and at least second elongate members are in mating engagement, the male component of the first elongate member is received by the female component of the at least second elongate member and the female component of the first elongate member receives the male component of said at least second elongate member; and wherein said first and at least second elongate members are longitudinally moveable relative to the other.

The bone fixation region of at least one elongate member may be adjacent to the first end. The mating region typically extends from said bone fixation region to a second end of the elongate member.

The mating regions of the elongate members may be substantially identical to one another. In one embodiment, at least the mating regions the first and at least second elongate members are identical to each other. When in mating engagement, the mating regions of the elongate members may comprise mirror images of each other.

The elongate members may be slidably, longitudinally moveable relative to one another.

The elongate members when connected to each other are substantially not rotationally moveable relative to each other. Further, each elongate member is typically not translationally moveable to the other elongate member.

Two elongate members may be assembled together initially by bringing the respective second ends of each elongate member into engagement. The configuration of the two elongate members may be such that a slidable interlock is formed therebetween and the second end of the first elongate member and the second end of the at least second elongate member may be longitudinally moved along the mating region of the other elongate member and towards the fixation region of the other elongate member.

In one assembly, the two elongate members are in full mating engagement with the first end of the first elongate member opposite to the first end of the at least second elongate member, the majority of the length of each elongate member being in mating engagement with the other elongate member. In this configuration, the mating interlock zone comprises substantially all of the mating region of each elongate body. Typically, the device of the present disclosure is introduced into a target site in a body of a patient in said full mating engagement assembly.

The mating between the two elongate members allows for relative longitudinal movement and thus when one elongate member is moved relative to the other or both are moved relative to each other in an opposite direction, the mating interlock zone is incrementally reduced in length, while the entire assembly of both elongate members increases in length.

As one or both of the elongate members move in opposite directions longitudinally, the assembly moves from said full mating engagement into partial mating engagement. The assembly of the two elongate members may transition gradually from full to partial mating dependent upon the driver of the movement.

Typically the bone fixation regions of the first and at least second elongate members are fixed to respective, opposed, bone regions such that when the bone grows, the elongate members are "pulled apart" and from the full mating engagement relative to each other to a partial mating engagement. Depending on the degree of growth of the bone, the mating interlock zone may decrease incrementally at least until the bone ceases to grow. In some instances, the device may be replaced with a replacement device once a certain length has been achieved.

The device may also including a locking mechanism to lock the elongate members in place once the desired bone growth is achieved i.e., when the bone has stopped growing. The locking mechanism may include a number of structures such as a clamp to clamp the first and at least second elongate member together. Still further, the first and at least second elongate members may comprise an aperture to receive a pin therethrough. Said pin may fix each elongate member to the bone and hold it in place following full bone growth.

The elongate members of the present disclosure may be made from a number of biocompatible materials. The elongate members may be made from a metal or a metal alloy or alternatively may be made from a polymeric material. Examples of suitable materials include stainless steel and its alloys, titanium and its alloys, cobalt chrome and its alloys, tantalum and its alloys, polyether ether ketone (PEEK), MP35N and its alloys, graphite/pyrocarbon.

Each elongate member may be substantially straight and extend from the first end to said second end. The cross section of the bone fixation region may differ relative to the cross section of the mating region.

The fixation regions may comprise a number of different structures. The bone fixation device may be circular in cross section. Alternatively, the bone fixation region may comprise a flattened plate, an ovoid, square, or elliptical cross section. Still further, the bone fixation region may include a threaded outer surface.

In another embodiment, the bone fixation region may comprise a roughened, etched, porous or ribbed surface for bone and tissue ingrowth and to promote bone fixation for subsequent development of mechanical fixation. The bone fixation region may include a coating or be impregnated with an agent to promote bone fixation. In one embodiment, the surface of the bone fixation region may include a Hydroxyapatite (HA) coating. In this regard, the surface may be a beaded porous surface, wire mesh porous surface, selective sintered porous surface or other trabecularized metal scaffold.

The surface of device of the present disclosure may be coated for drug elution. In this regard, the surface may be coated for the elution of any one or more of the following: antibiotics, antimicrobials, an osteoinductive agent (including but not limited to an osteogenic protein, or a growth factor, or a member or the TGF-beta superfamily). Preferably the osteoinductive agent is an osteogenic protein. Preferably the osteogenic protein is a bone morphogenetic protein (BMP), preferably recombinant human form selected from rhBMP-1, rhBMP-2, rhBMP-3, rhBMP-4, rhBMP-5, rhBMP-6, rhBMP-7, rhBMP-8a, rhBMP-8b, rhBMP-9, rhBMP-10, and rhBMP-15. More preferably the BMP is rhBMP-2 or rhBMP-7.

In one embodiment, the osteogenic protein is rhBMP-2. In other preferred embodiments, suitable osteogenic proteins include rhBMP-7 (OP-1) currently approved for clinical use, rhBMP-4, rhBMP-6, and rhBMP-9 are other preferred embodiments.

In another embodiment, the eluted agent acts via the wnt pathway. Agents such as antibodies to sclerostin. Dkk1 and Dkk2, SFRP1 and SFRP2 are envisaged. Antibodies that augment the wnt pathway via LRP 4 5 or 6 could also be eluted. In one embodiment, small molecule drugs such as GSK3 antagonists such as lithium and its salts and AR28 (AZD9828) and related compounds may also be eluted to upregulate wnt pathway activity.

In other embodiments the osteoinductive agent may be a growth factor such as platelets/platelet derived growth factor (PDGF), insulin-like growth factor (IGF), vascular endothelial growth factor (VEGF), and/or a member of the TGF-beta superfamily such as TGF-beta 1, TGF-beta 2, TGF-beta 3, growth and differentiation factors (GDFs), fibroblast growth factors, activins, inhibins, or other specific activators of these pathways. The active agent may also comprise additional agents such as the Hedgehog, Frazzled, Chordin, Noggin, Cerberus and Follistatin proteins, or small molecule, protein, or antibody-based agents that antagonize Dickkhopf-1, Sclerostin, or other member of the Wrint signalling pathway. The active agent may also include antibodies, peptides, or soluble receptors affecting these pathways (tyrosine kinase growth factor receptors, insulin receptors, activin-like kinase receptors, bone morphogenetic protein receptors, fibroblast growth factor receptors, and transforming growth factor receptors) in full length, truncated, or with point mutations. In a preferred embodiment the factor that is antagonized is Myostatin (GDF-8).

In other embodiments, agents known to bone and effect the delivery and presentation of growth factors to cells are included or added. Such agents include heparin sulphate and other glycosaminoglycans and their components, as well as specific binding proteins such as TGF-β binding protein.

In another embodiment the eluted agent is an anti-resorptive agent. Preferred anti-resorptive agents include bisphosphonates such as zoledronic acid, pamidronic acid, ibandronic acid, etidronic acid, alendronic acid, risedronic acid, or tilurondic acid as well as other non-specified bisphosphonates or their salts. Other anti-resorptive agents include IKK inhibitors (such as PS-1145), Osteoprotegerin (OPG), inhibitors of Cathepsin K, Chloride Ion Channel Blockers, Proton pump inhibitors, and antagonists of RANKL (Denosumab), and others.

In one embodiment, the bone fixation region includes at least one aperture which extends transversely across the elongate body said aperture configured to receive a locking member to lock said elongate member to a bone. In this embodiment, examples of a locking member include locking pins, screws, bolts or K-wires.

In another embodiment, the bone fixation region includes at least a pair of opposed slots formed in the elongate member. The slots of this embodiment are configured to receive a locking peg to substantially fix the elongate member to the bone.

In a further embodiment, at least one end of the elongate members may include a locking head which is configured to lock into a screw or other device to hold the elongate member in the bone.

At least one of the elongate members may include an angled portion adjacent to the first end. The angle formed between the angled portion and the remainder of the elongate member may be between about 1° and 15°. Preferably the angle is between 3° and 8°. More typically the angle is between 6° and 7°. This angle is designed to allow for optimal entry to the bone. In one embodiment, the angled portion includes the bone fixation region of the elongate member. The angled portion of the elongate member is particularly suitable for trochanteric entry into a bone of a subject.

Further, the devices of the present disclosure may utilise a motor to actively extend the elongate members. Examples of the type of "motor" include but are not limited to a manual expansion: a simple mechanical device such as a spring or clockwork device; an osmotic pump device; a programmable electric motor; a motor powered by external ultrasound energy; a magnetic motor. In one embodiment, the motor may be an external fixator, either monolateral or ring device.

The term "non-telescopically arranged" is intended to differentiate from tubular members wherein one relatively smaller diametered tubular member is insertable into the lumen of a larger diametered, second tubular member.

Throughout this specification the word "comprise", or variations such as "comprises" or "comprising", will be understood to imply the inclusion of a stated element, integer or step, or group of elements, integers or steps, but not the exclusion of any other element, integer or step, or group of elements, integers or steps.

BRIEF DESCRIPTION OF THE DRAWINGS

By way of example only, embodiments are now described with reference to the accompanying drawings, in which:

FIG. 2a is a cross sectional view of the device of FIG. 2 where the two elongate members are in mating engagement;

FIG. 3a is a cross sectional view of the device of FIG. 3 where the two elongate members are in mating engagement;

FIGS. 6a and 6b show different perspective views of a device according to another embodiment of the present disclosure;

FIG. 6c is a cross sectional view of the device of FIG. 6a;

FIG. 15a depicts another embodiment of the device for use in a spinal distraction procedure;

FIG. 15b is a cross sectional view of the device of FIG. 15a;

FIGS. 18a to 18c show side and perspective views of another embodiment of the device;

FIG. 18d is a cross sectional view of the device of FIGS. 18a to 18c;

FIG. 19b is a top view of the device of the embodiment of FIG. 19a;

FIG. 25a depicts a spine with an embodiment of the device attached;

FIGS. 25b to 25d show an embodiment of the device for use in spinal stabilisation as a child grows;

FIGS. 26a to 26c depict various views of a device for use in rib stabilisation;

DESCRIPTION OF EXEMPLARY EMBODIMENTS OF THE DISCLOSURE

An orthopaedic device of the present disclosure is generally shown as 10 in the attached drawings. The device 10 is used for securing to a bone of a subject to aid in stabilising and in some cases lengthening of a bone as discussed further below.

Figures 1, 1A:
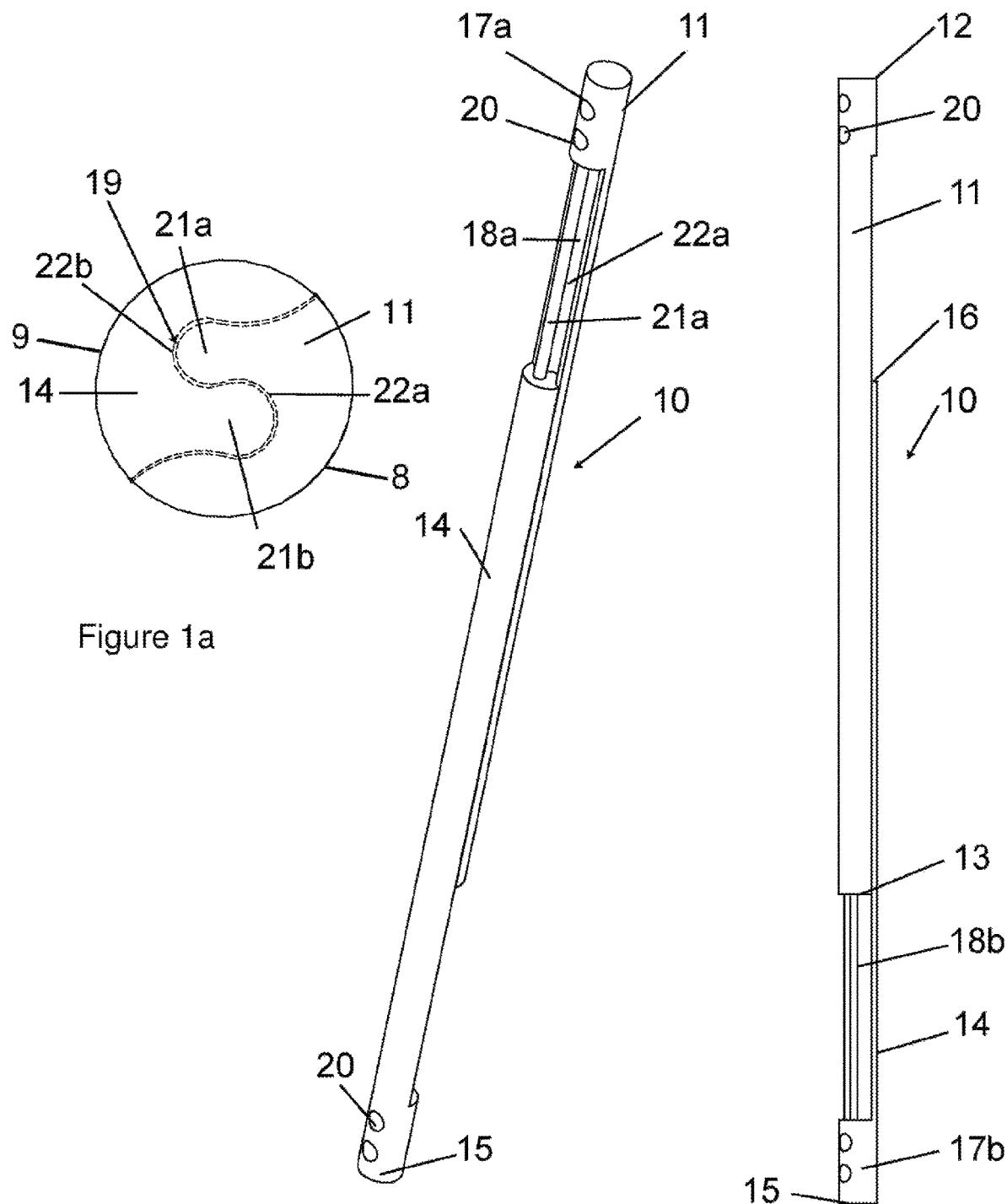
FIG. 1 shows two different perspective views of a device according to an embodiment of the present disclosure.
FIG. 1a is a cross sectional view of the device of FIG. 1 where the two elongate members are in mating engagement.

The device 10 includes a first elongate member 11 which extends from a first end 12 to a second end 13. As shown in FIG. 1, device 10 also includes a second elongate member 14 which also extends from a first end 15 to a second end 16.

First elongate member 11 has a first bone fixation region 17a and a first mating surface 18a. Second elongate member 14 has a second bone fixation region 17b and a second mating surface 18b. First mating surface 18a is configured for engagement with second mating surface 18b to form a mating interface 19 which can be seen in the cross section view of, for example, FIGS. 1a, 2a, 3a.

First elongate member 11 and second elongate member 14 are longitudinally moveable relative to each other but can be engaged with each other as shown such that device 10 is rotationally and translationally stable.

In the embodiments depicted, for example in FIGS. 1 and 1a, the configuration of the two elongate members 11, 14 is such that they have a nested geometry and the mating interface 19 between the two elongate members dissects the device 10 axially.

First elongate member 11 has both a first elongate ridge 21a and a first elongate groove 22a. Similarly, second elongate member 14 has a second elongate ridge 21b and a second elongate groove 22b. While in FIG. 1a, a small space is depicted between the two elongate members 11, 14, this is simply to show the elongate ridges 21a, 21b and elongate grooves 22a, 22b more clearly and, in use, the two elongate members 11, 14 are typically in tight abutment when mated together along the mating interface 19.

The interdigitation of the elongate ridges 21a, 21b and elongate grooves 22a, 22b of the mating surfaces provides a rotational lock for each elongate member relative to the other. Further, translational movement is not possible given the interdigitating nature of the mating. Only longitudinal movement of each elongate member relative to the other is possible when the elongate members are assembled as shown in, for example FIG. 1.

The geometry of the elongate ridges 21a, 21b and elongate grooves 22a, 22b may vary as depicted in the drawings. In several embodiments, first elongate ridge 21a extends into a relatively bulbous end with a relatively narrower neck. Part of the bulbous end of elongate first ridge 21a defines one side of the opening of first elongate groove 22a. Similarly, second elongate ridge 21b comprises a relatively bulbous end defining part of the opening of second elongate groove 22b. It can be seen in FIG. 1a that first elongate groove 22a is the inverse shape of second elongate ridge 21b such that second elongate ridge 21b may be nested within first elongate groove 22a. Likewise, second elongate groove 22b is the inverse shape of first elongate ridge 21a and thus first elongate ridge 21a may be nested within second elongate groove 22b.

The overall configuration of the first mating surface 18a of first elongate member 11 of an embodiment such as depicted in FIGS. 1 and 1a is a mirror image of second mating surface 18b of second elongate member 14.

Figure 2:
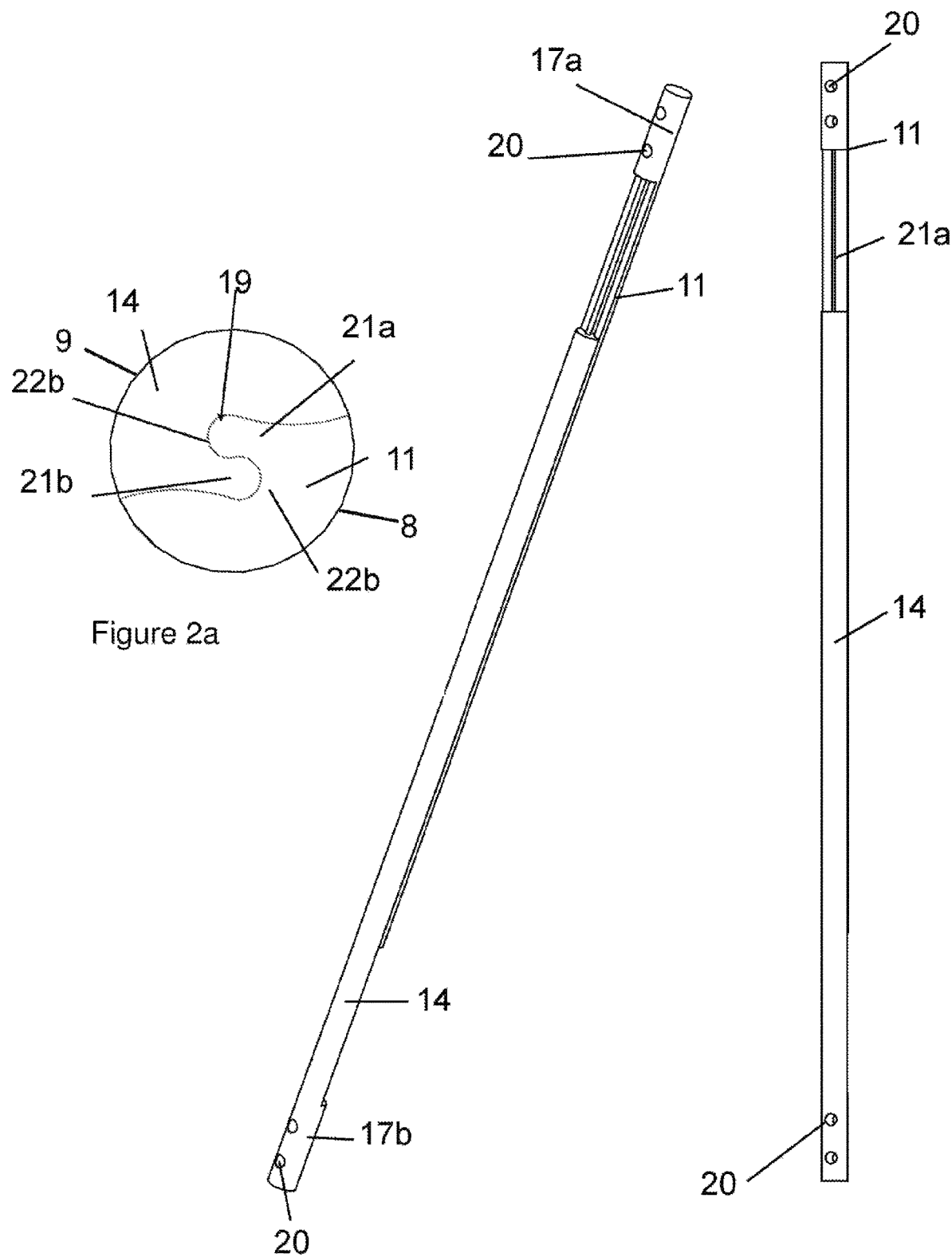
FIG. 2 shows two different perspective views of a device according to another embodiment of the present disclosure.
Figure 3:
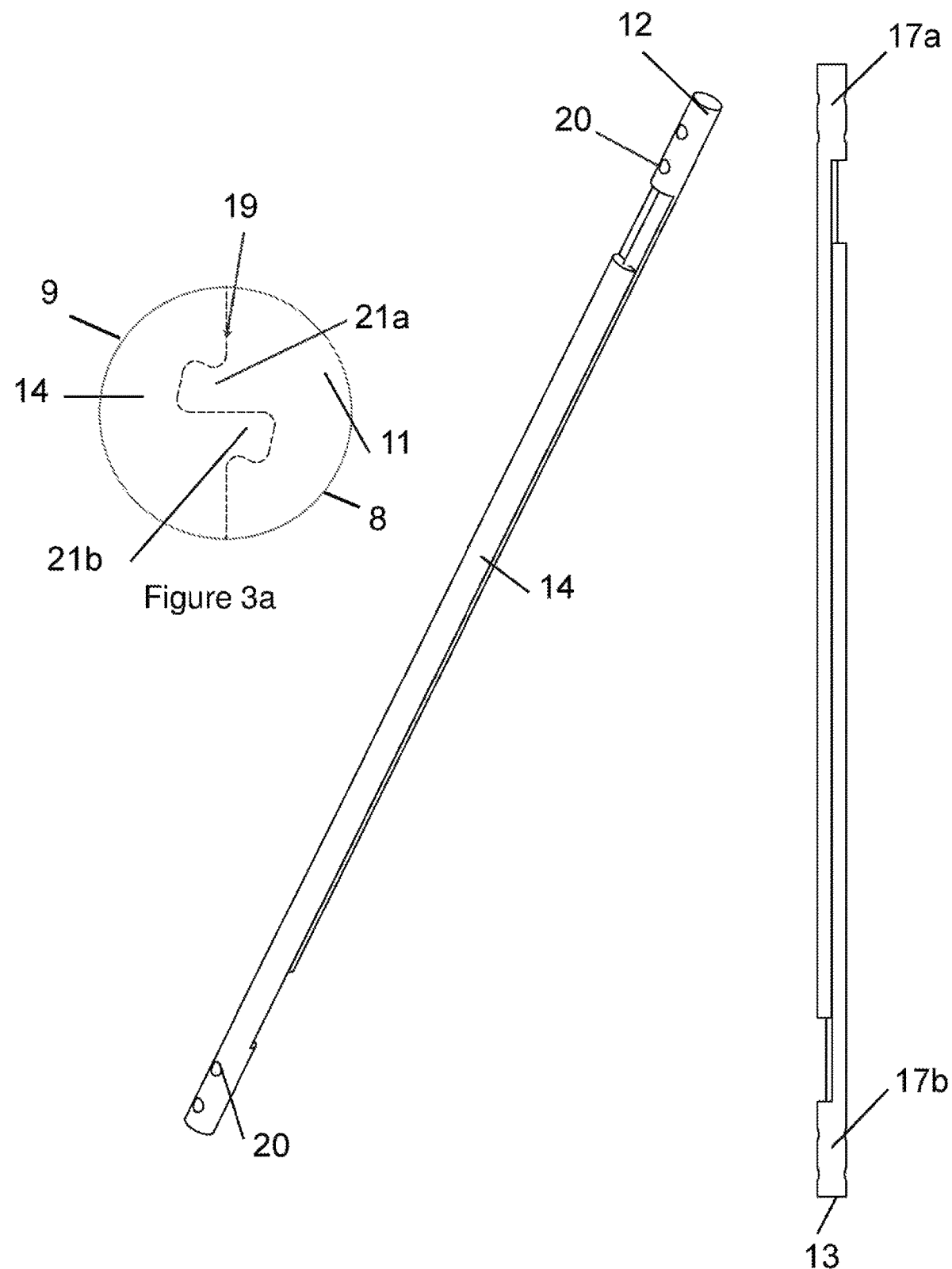
FIG. 3 shows two different perspective views of a device according to another embodiment of the present disclosure.

FIGS. 2 and 2a show a similar configuration to the embodiment of FIGS. 1 and 1a but where the elongate ridges 21a, 21b and elongate grooves 22a, 22b are relatively smaller in dimensions than those shown in FIG. 1a.

Figures 4, 4A:
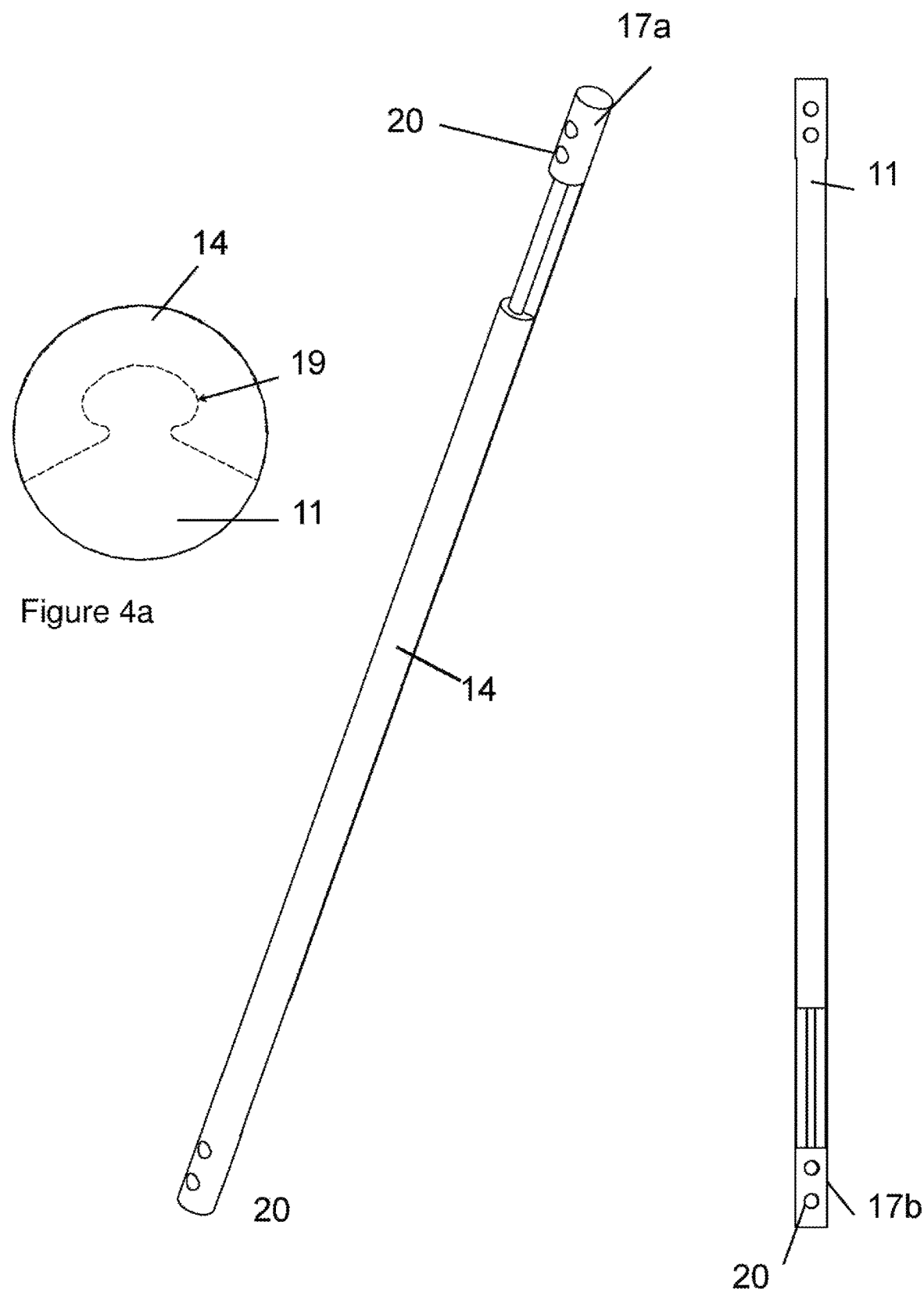
FIG. 4 shows two different perspective views of a device according to another embodiment of the present disclosure.
FIG. 4a is a cross sectional view of the device of FIG. 4 where the two elongate members are in mating engagement.

In FIG. 3a, first elongate ridge 21a and second elongate ridge 21b each have a relatively straight side although both still form a relatively bulbous end and have a relatively narrower neck. FIG. 4a shows an embodiment in cross section which has a mortar and tenon design.

While many designs are envisaged, it is preferred that both the first elongate member 11 and the second elongate member 14 have the same moment of inertia in all planes relative to each other such as to provide an equally stable structure relative to the bone as the two elongate members are extended with growth of the bone.

Because, the two elongate members 11, 14 of device 10 are not in a traditional telescoping arrangement they are able to engage each other to provide rotational and translational stability as depicted through the interdigitational alignment but at the same time facilitate longitudinal movement of elongate member 11 and 14 relative to each other.

First bone engagement region 17a is positioned at first end 12 of first elongate member 11. Second bone engagement region 17b is positioned at first end 15 of the second elongate member 14. As discussed above, when brought into mating engagement such as depicted in FIGS. 1 and 2, the first and second elongate members are slidably, longitudinally moveable relative to one another but substantially not rotationally moveable relative to each other.

A first elongate member 11 and a second elongate member 14 may be assembled together initially by bringing second end 13 of first elongate member 11 into engagement with second end 16 of the second elongate member 14. The mating surfaces 18a and 18b may, in certain embodiments as depicted in FIGS. 1, 1a, 2 and 2a, be the mirror image of each other. Therefore, first elongate ridge 21a may be slid into the inversely shaped second elongate groove 22b; and second elongate ridge 21b slid into first elongate groove 22a. During assembly, each elongate ridge may be slid the entire length of their respective elongate groove to form an insertion assembly device 10 having a first insertion length n. When the assembly is implanted in a bone of a subject, the elongate members 11, 14 move relatively apart over time such that the overall length of the assembly increases to greater than n.

In the insertion assembly of device 10 mating surface 18a is in full mating engagement with mating surface 18b, that is, the entire length of first elongate ridge 21a is nested along the entire length of second elongate groove 22b and the entire length of second elongate ridge 21b is nested along the entire length of first elongate groove 22a. Longitudinal movement of the elongate members as discussed, moves the elongate members from full mating engagement into partial mating engagement (see for example the positioning of the elongate members relative to each other in FIG. 1).

Figure 14A:
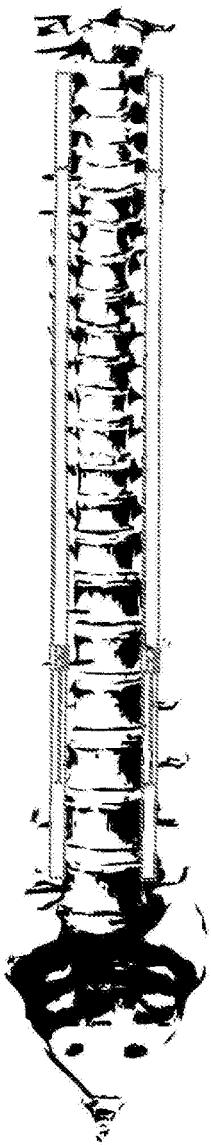
FIG. 14a depicts a spine with device 10 in place.
Figure 14B:
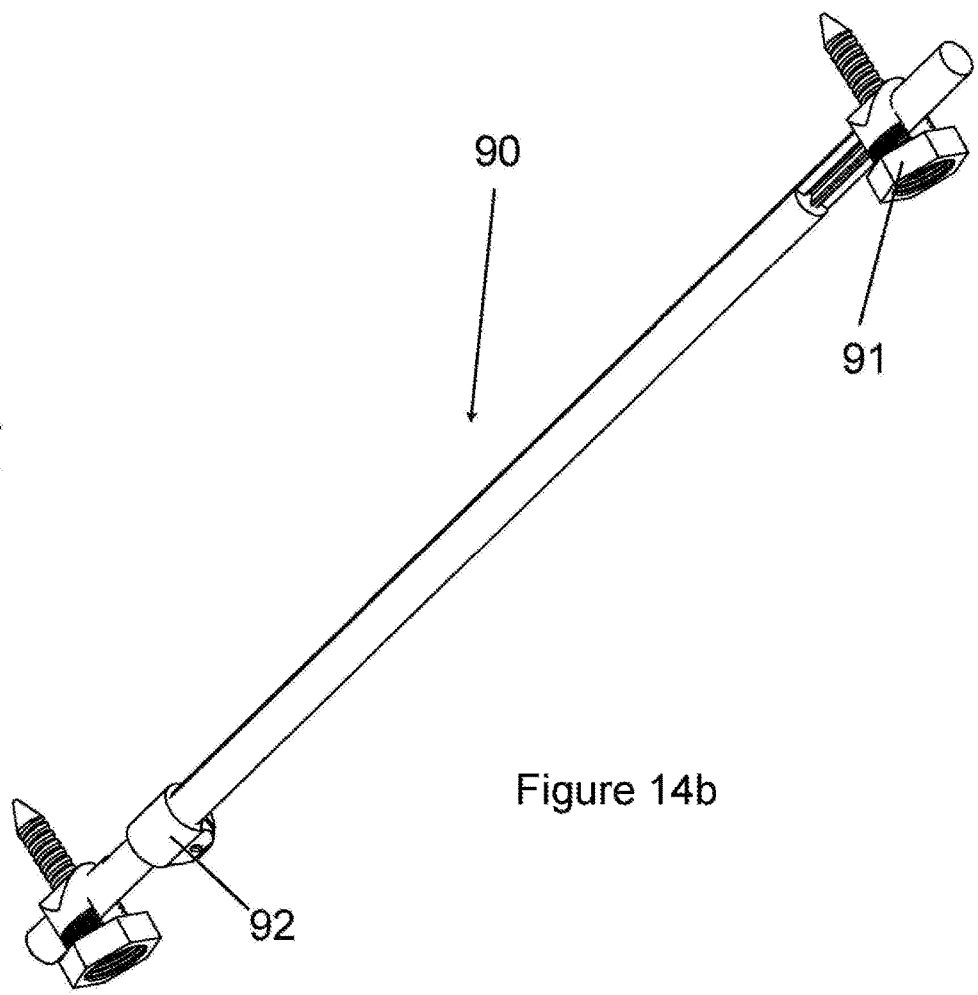
FIG. 14b depicts the device 10 for use in a conventional distraction procedure of the spine.

Device 10 includes a locking mechanism to lock the elongate members 11, 14 in place once the desired bone growth is achieved. The locking mechanism may include a number of structures such as a clamp 92, shown in FIG. 14b. Clamp 92 clamps the first and at least second elongate member together. Clamp 92 is suitably sized and shaped to fit around the outer circumference of the elongate bodies 11, 14 when mated together. Clamp 92 may be secured by a pin, screw or bolt.

Figure 9:
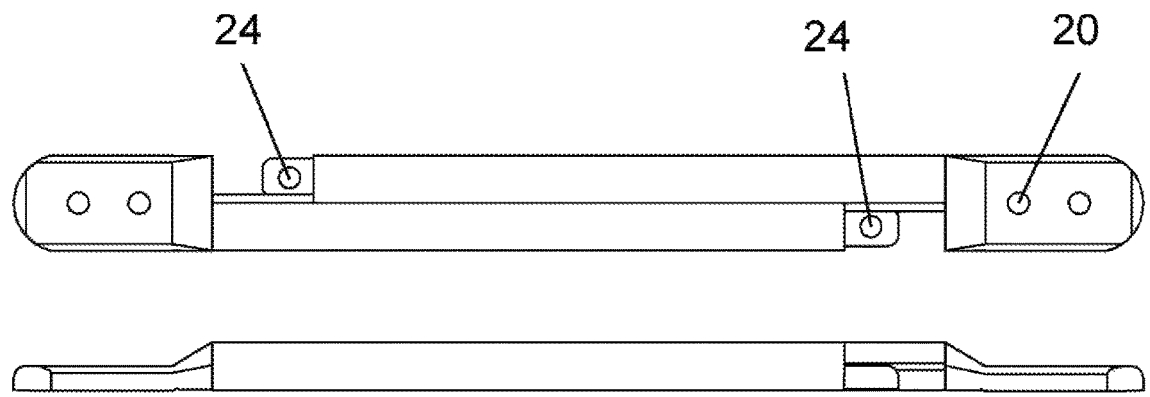
FIG. 9 is a top and a side view of another embodiment of the device of the present disclosure.
Figure 10A:
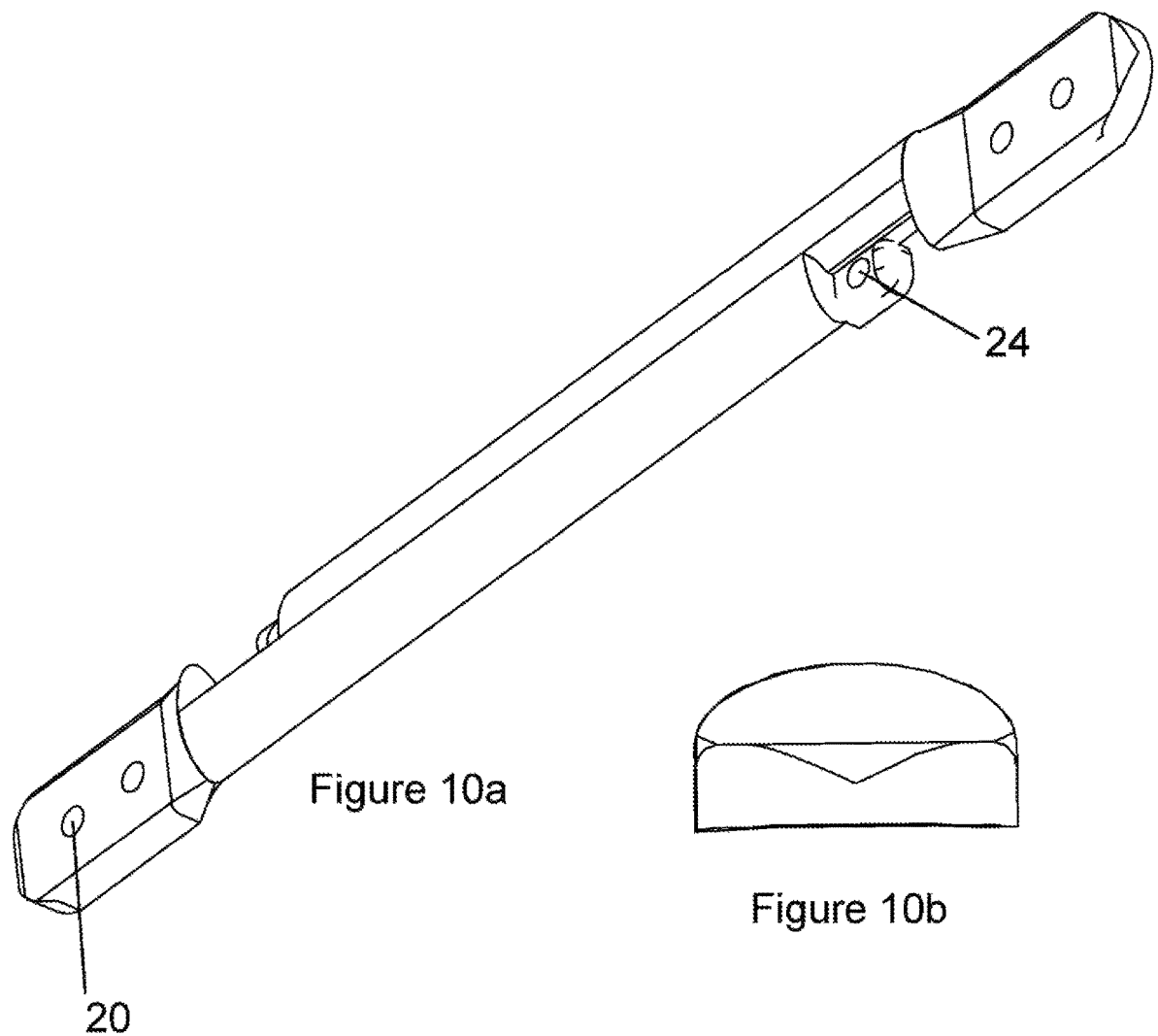
FIG. 10a is a perspective view of the device of FIG. 9.

Alternatively, the locking mechanism may comprise an aperture in the first and at least second elongate members 11, 14 such as aperture 24 depicted in FIGS. 9 and 10. The aperture 24 is configured to receive a pin, screw, K wire or other locking device (not shown) therethrough to fix each elongate member to the bone and hold it in place following full bone growth.

Figures 5, 5A, 5B:
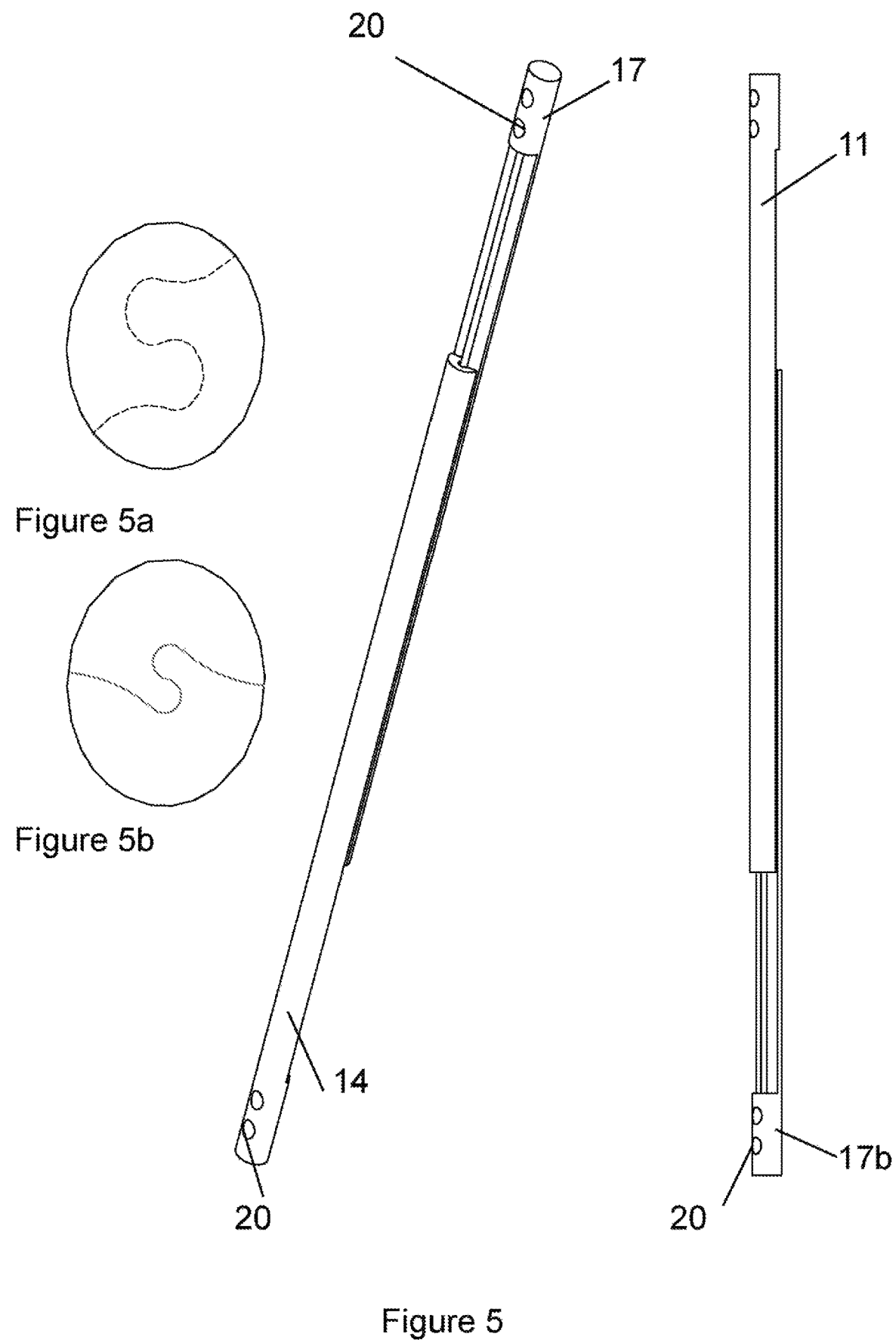
FIG. 5 shows two different perspective views of a device according to another embodiment of the present disclosure.
FIGS. 5a and 5b show alternative cross sectional arrangements of the device of FIG. 5.
Figures 6A, 6B, 6C:
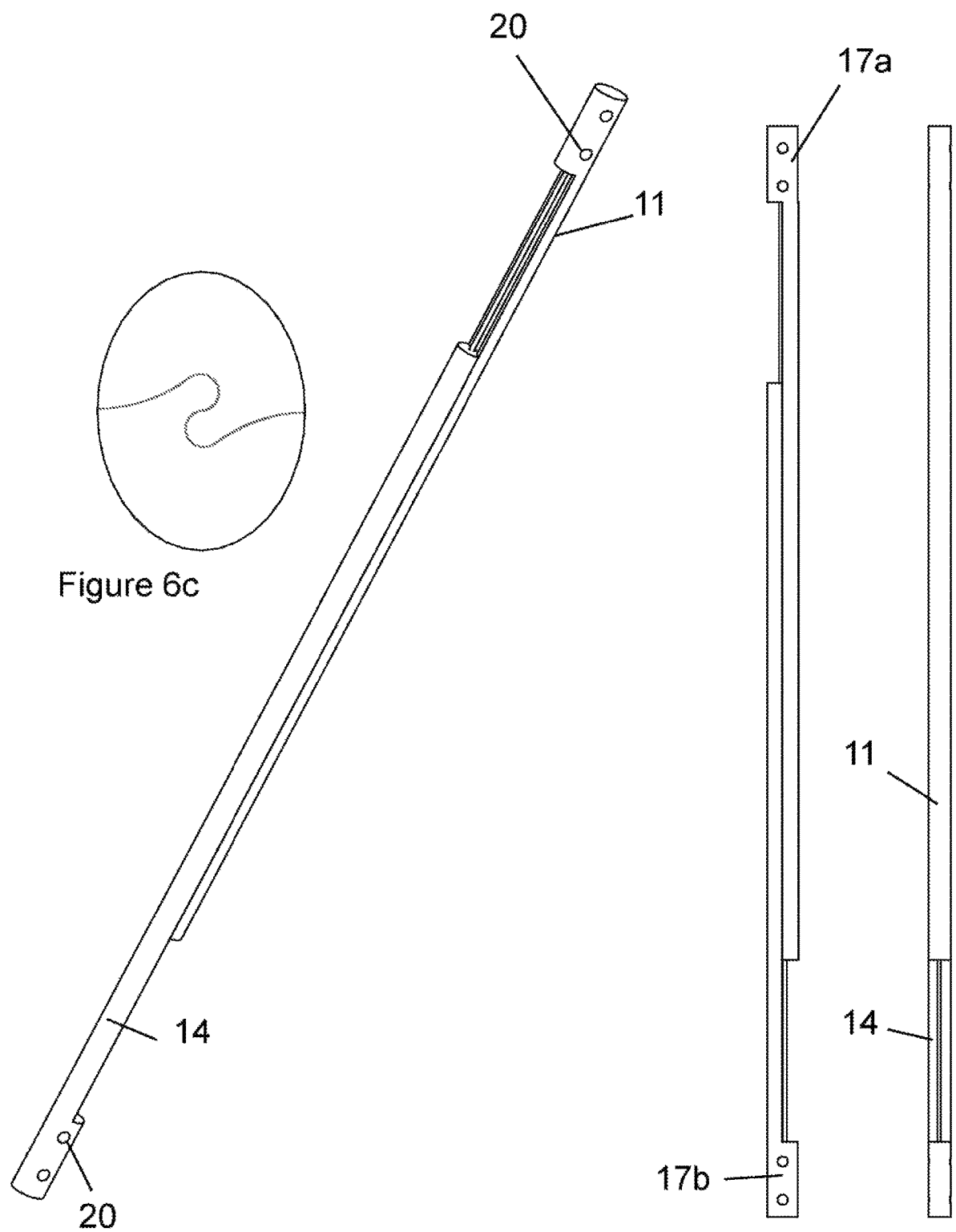

The device 10, as shown in, for example, FIG. 1 has a circular cross section when the two elongate members 11, 14 are mated together as shown in FIG. 1a. Other cross sections may be desirable depending upon the application of the device 10 and could be, for example oval such as depicted in FIGS. 5a and 5b.

The bone fixation regions 17a and 17b are larger in diameter than the remainder of each elongate member 11 and 14 i.e. larger in diameter than mating surfaces 18a, 18b as shown in FIG. 1. But when the two elongate members 11 and 14 are mated together the resultant assembly has the same diameter as the bone fixation regions 17a and 17b. This affords a relatively streamlined assembly which is easy to insert into the bone of a subject and avoids any edges or corners which could damage surrounding bone.

First elongate member 11 has both a first mating surface 18a and a first non-mating surface 8. Similarly, second elongate member 14 has a second mating surface 18b and a second non-mating surface 9. As shown in the embodiments of FIGS. 1a, 2a and 3a first non-mating surface 8 is identical to second non-mating surface 9.

Each bone fixation region 17a and 17b includes a means to secure the elongate members 11 and 14 to the surrounding bone. While this may be achieved by a number of mechanisms, one embodiment as shown in FIGS. 1 to 6 includes one or more holes formed through the bone fixation regions 17a and 17b. In this way, a pin, screw, K wire or other locking device may be inserted through said holes 20 to hold the device 10 in place.

Figure 17:
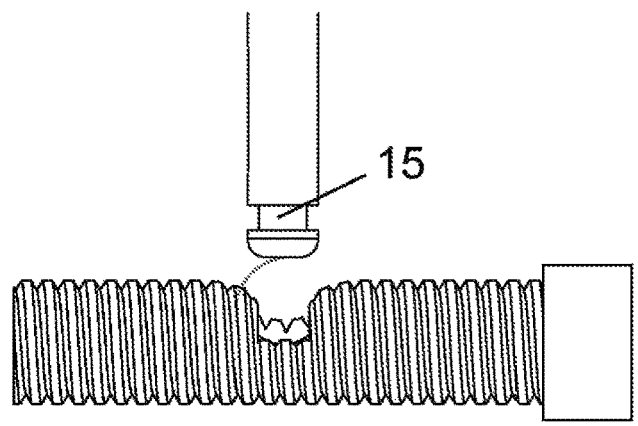
Figure 19A:
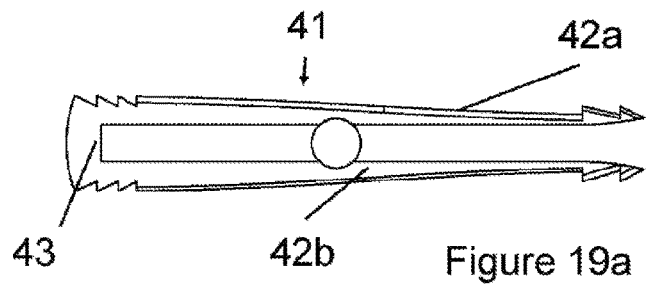
FIG. 19a is a top view of one embodiment of the device with a clip device in place.
Figure 19B:
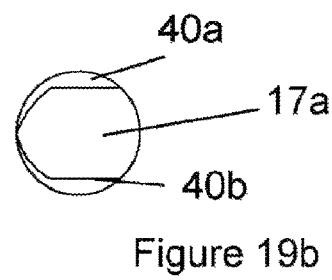
Figure 20A:
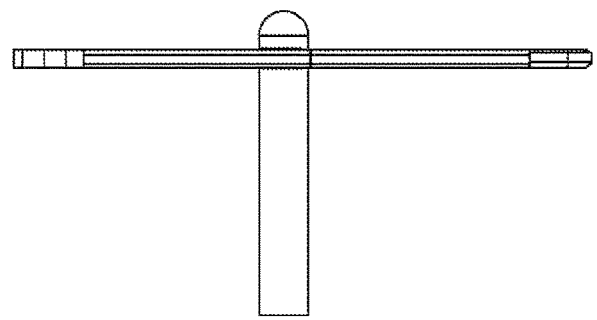
FIGS. 20a and 20b, 21a and 21b are side and perspective views of the device of the embodiment of FIGS. 19a and 19b, with and without a clip in place.
Figure 20B:
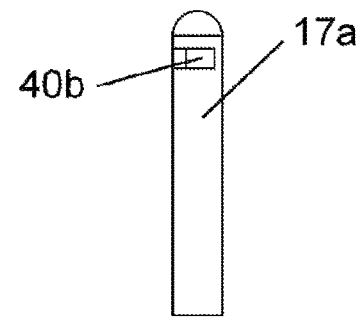
Figure 21A:
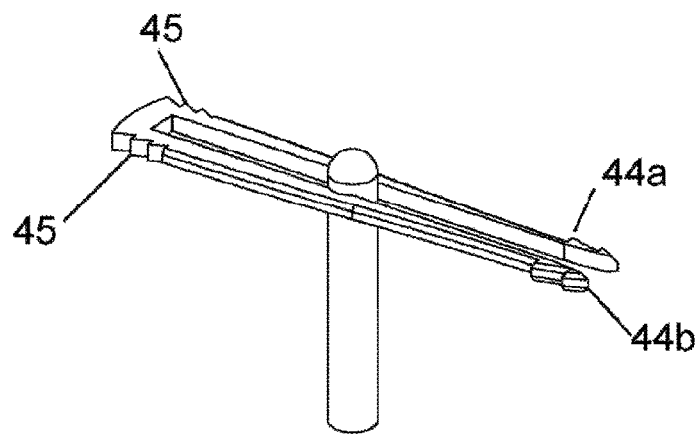
Figure 21B:
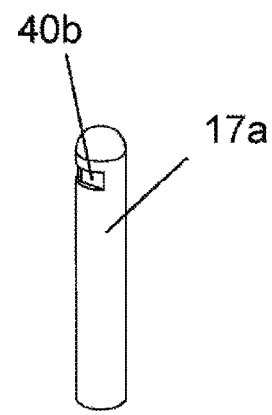

For small sized embodiments of device 10, it is often not feasible to pin across an aperture or the like and instead, the end 15 of device 10 may be locked into a cross screw 100 which has a receiving aperture 101. Cross screw 100 includes screw thread 102 to secure into the surrounding bone as shown in FIG. 17a.

In another embodiment of a device generally depicted as 110 in FIGS. 18a to 18d, the device has two opposed screw threaded bone fixation portions 111 and 112 to screw into the surrounding bone. This device 110 can be used with a guidewire system and as such includes a central lumen 113 which extends along the length of the device. In the embodiment depicted, portion 111 has a coarser thread than portion 112. Portion 111 may also have a wider diameter than portion 112.

This embodiment may be of particular use in conditions such as slipped capital femoral epiphysis or as prophylaxis for slipped capital femoral epiphysis. Alternatively it may be used as an intramedullary device in a long bone.

Figures 27A, 27B, 27C:
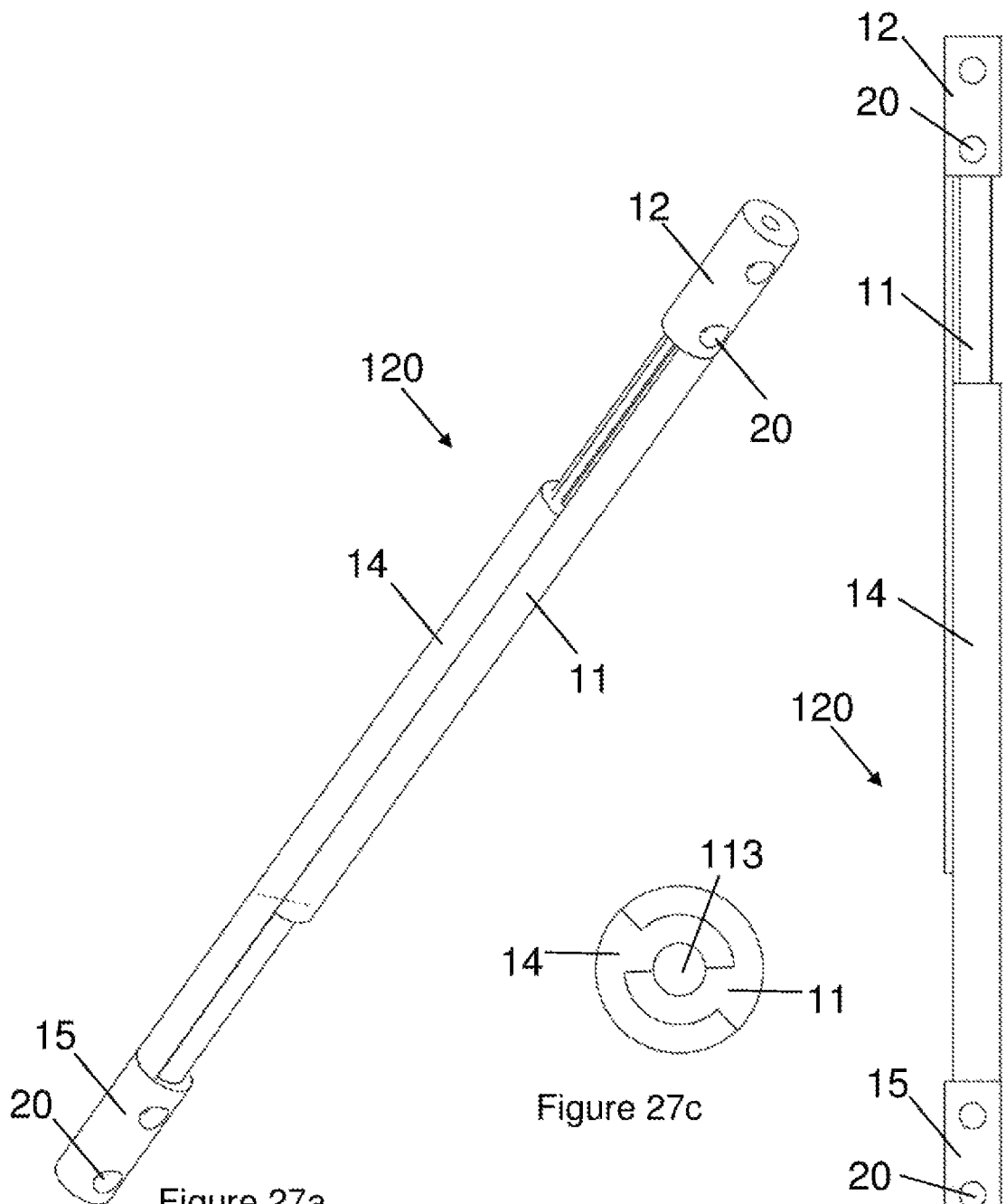
FIGS. 27a and 27b show two different perspective views of a device according to another embodiment of the present disclosure.
FIG. 27c is a cross sectional view of the device of FIG. 27a where the two elongate members are in mating engagement.
Figure 27D:
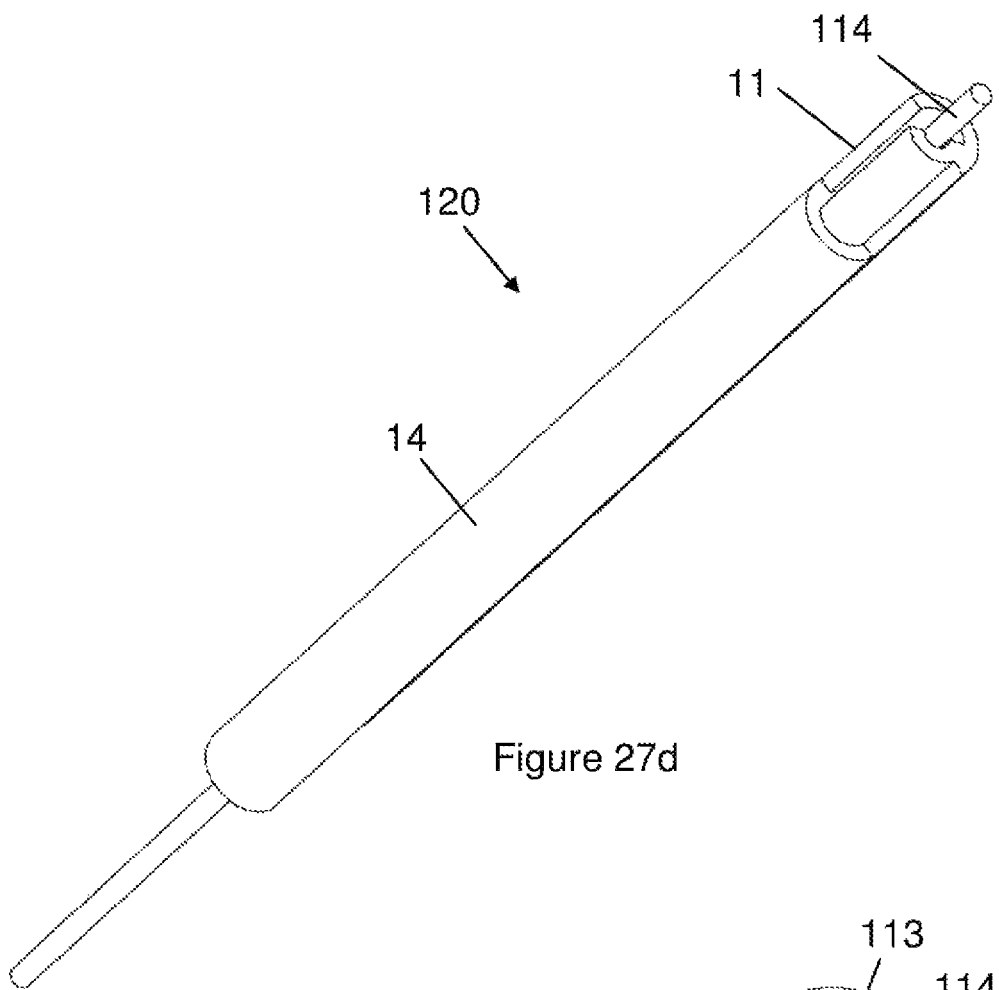
FIG. 27d is a perspective view of the device of FIG. 27a positioned over a guidewire.
Figure 27E:
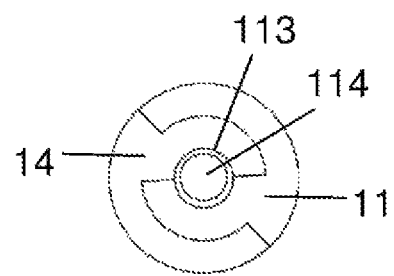
FIG. 27e is a cross sectional view of the device of FIG. 27d where the two elongate members are in mating engagement.

Although the device depicted as 110 in FIGS. 18a to 18d utilises a central lumen 113 in conjunction with screw threaded bone fixation portions 111 and 112, the device 110 may take a variety of other configurations. For example, it need not include screw threaded bone fixation portions at ends of the device 110. In this regard, the device 110 can be modified in accordance with the device generally depicted as 120 in FIGS. 27a to 27c, for example. This device includes ends 12, 15 similar to device 10 depicted in FIGS. 1 to 6b. FIGS. 27d and 27e illustrate how the device 120 can be used with a guidewire system, in particular where a guidewire 114 extends through the central lumen 113. To aid visibility, the ends 12, 15 are omitted from the device 120 as depicted in FIGS. 27d and 27e.

As for devices 110 and 120, device 10 may also include a central lumen extending along the length of the device. In such embodiments, first elongate ridge 21a and second elongate ridge 21b may be modified to define part of the aperture. Similarly, the opening of elongate grooves 22a and 22b may be similarly modified to define a further part of the aperture. In combination, ridges 21a, 21b and grooves 22a and 22b may together define the shape of the aperture.

Figures 28A, 28B, 28C:
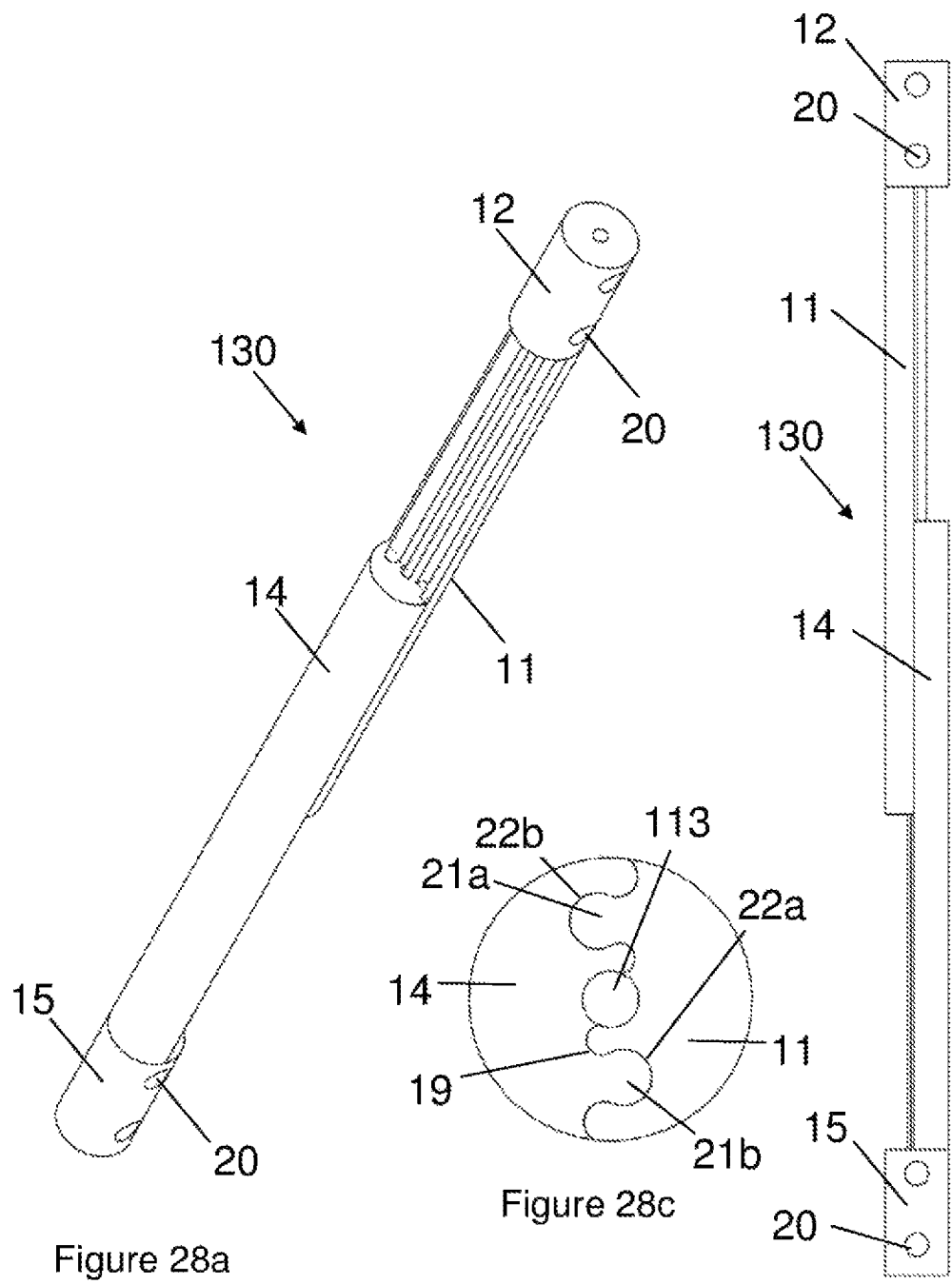
FIGS. 28a and 28b show two different perspective views of a device according to another embodiment of the present disclosure.
FIG. 28c is a cross sectional view of the device of FIG. 28a where the two elongate members are in mating engagement.
Figures 28D, 28E:
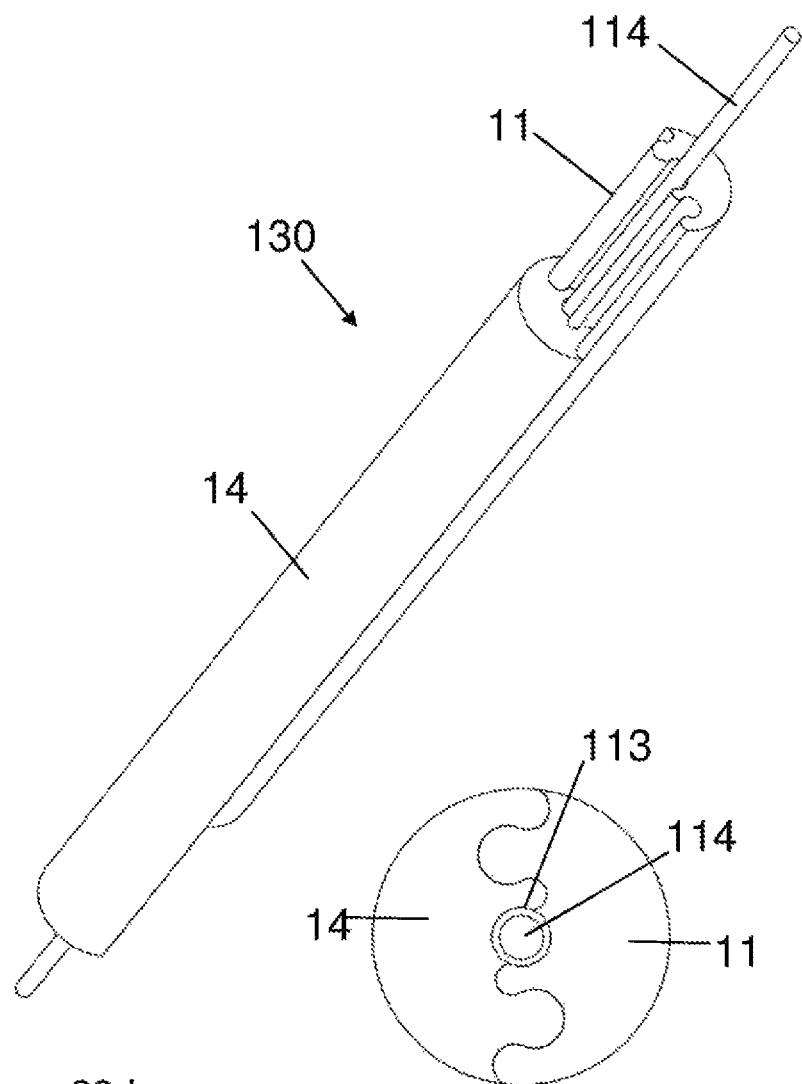
FIG. 28d is a perspective view of the device of FIG. 28a positioned over a guidewire.
FIG. 28e is a cross sectional view of the device of FIG. 28d where the two elongate members are in mating engagement.

Nevertheless, in one embodiment, in a device generally depicted as 130 in FIGS. 28a to 28c, the central lumen 113 is defined on the mating interface 19 between the first and second elongate members 11, 14, at a position between a first interdigitated ridge and groove pair 21a, 22b, and a second interdigitated ridge and groove pair 22b, 22a. The first and second interdigitated pairs are each spaced from the aperture of the central lumen 113 such that the inclusion of the central lumen 113 does not impair their engagement function. FIGS. 28d and 28e illustrate how the device 130 can be used with a guidewire system, in particular where a guidewire 114 extends through the central lumen 113. To aid visibility, the ends 12, 15 are omitted from the device 130 as depicted in FIGS. 28d and 28e.

Other mechanisms to hold the device 10 of the present disclosure in place within a bone are depicted in FIGS. 19 to 24. The embodiment depicted in FIGS. 19a to 21b include opposed slots 40a and 40b formed in bone fixation region 17a or 17b. Slots 40a and 40b receive a clip 41. Clip 41 comprises two arms 42a and 42b hingedly connected by a base 43. The arms 42a and 42b may be held in a biased configuration such that they are biased towards each other. In this manner, once aligned in the slots 40a and 40b, an inward pressure will retain clip 41 in position around bone fixation region 17a. Furthermore, ends 44a and 44b of arms 42a and 42b comprises a partially serrated or saw toothed outer surface to grip on to the surrounding bone and hold the clip thereto. Similarly, a region of the arms 42a and 42b located adjacent base 43 may also comprise an outer serrated or saw toothed surface 45 for similarly cutting into the surrounding bone.

Figure 22:
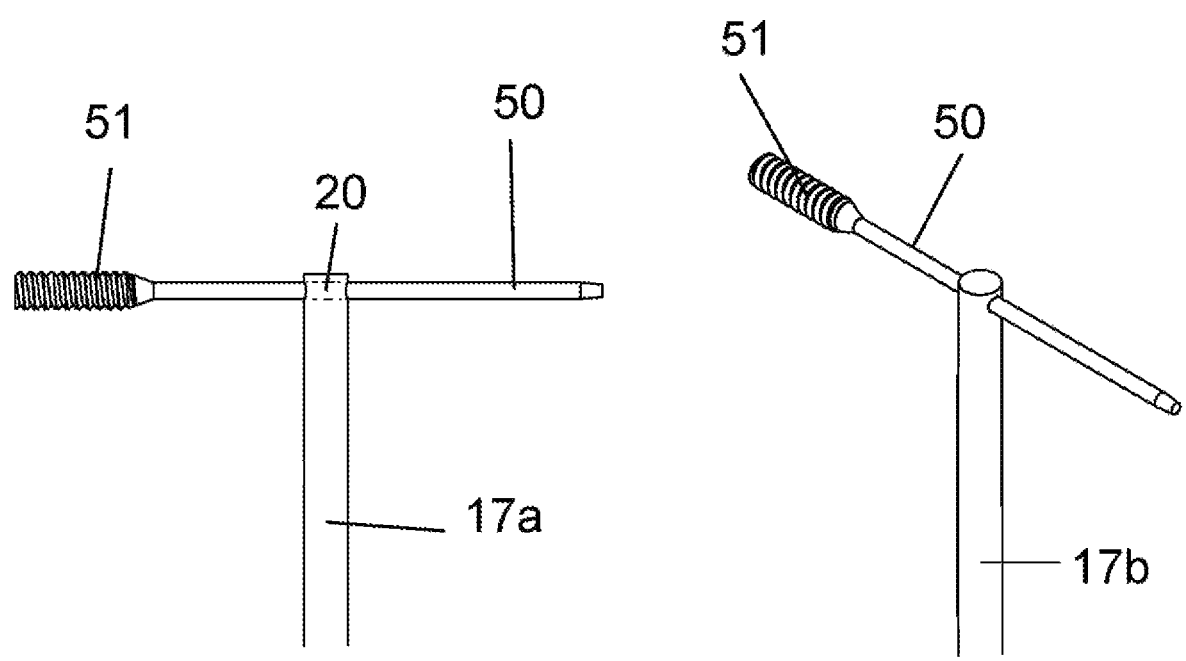
FIG. 22 shows perspective views of another bone locking arrangement.

FIG. 22 depicts an embodiment wherein a pin 50 is inserted through hole 20 of either bone fixation region 17a or 17b. For additional stability a proximal end 51 of pin 50 includes a proximal thread to screw into surrounding bone and lock the device 10 in place in the bone. This embodiment may be particularly useful for smaller devices 10.

Figure 23:
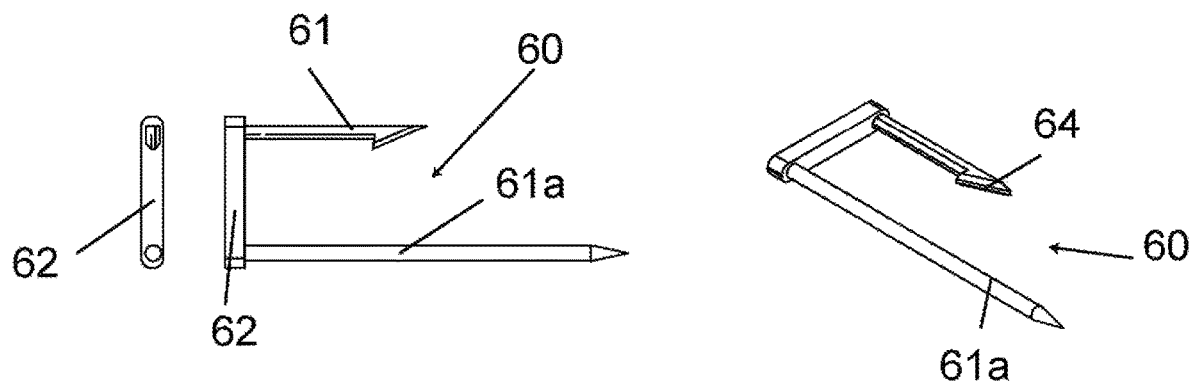
FIG. 23 and FIG. 24 show various views of still further bone locking arrangements.

In a further variation of the locking mechanism, FIG. 23 depicts a dident arrangement 60 having a main pin 61 which extends outwardly from a base plate 62 and adapted to extend through hole 20 of bone fixation region 17a or 17b. A smaller extension rod 61a extends from the base plate 62 in a spaced but parallel plane.

Extension rod 61a also includes an arrow head 64 which is configured to cut into surrounding bone to secure the device 10 in the bone.

Figure 24:
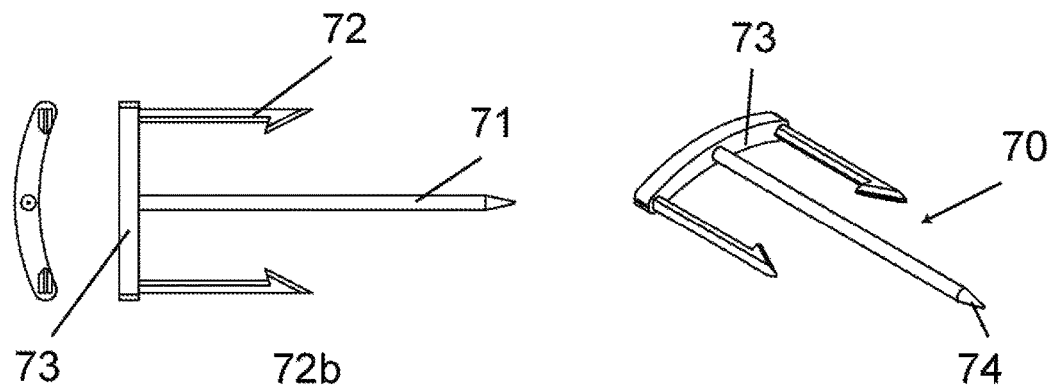

In FIG. 24, the locking device mechanism includes a trident structure 70 having a central rod 71 and two extension rods 72a and 72b which extend in spaced but parallel planes from a base plate 73. While the base plate may be any configuration including straight, the embodiment depicted shows a slightly curved base plate. The central rod 71 includes a distal tapered end 74 which is adapted to be inserted through hole 20 of bone fixation regions 17a and 17b. The extension rods 72a and 72b may also include an arrow head to cut into and grip surrounding bone.

Figure 10B:
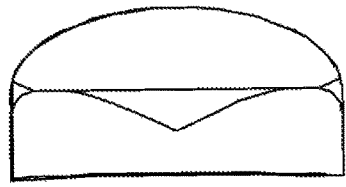
FIG. 10b is an end view of the device of FIG. 9.
Figure 11:
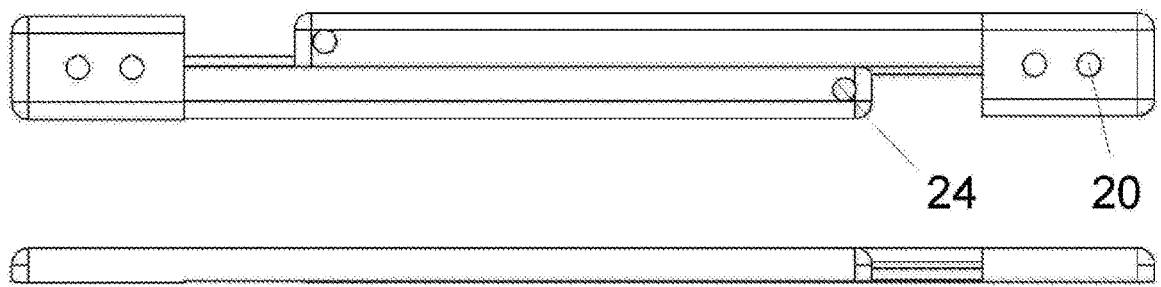
FIG. 11 is a top and a side view of another embodiment of the device of the present disclosure.
Figure 12:
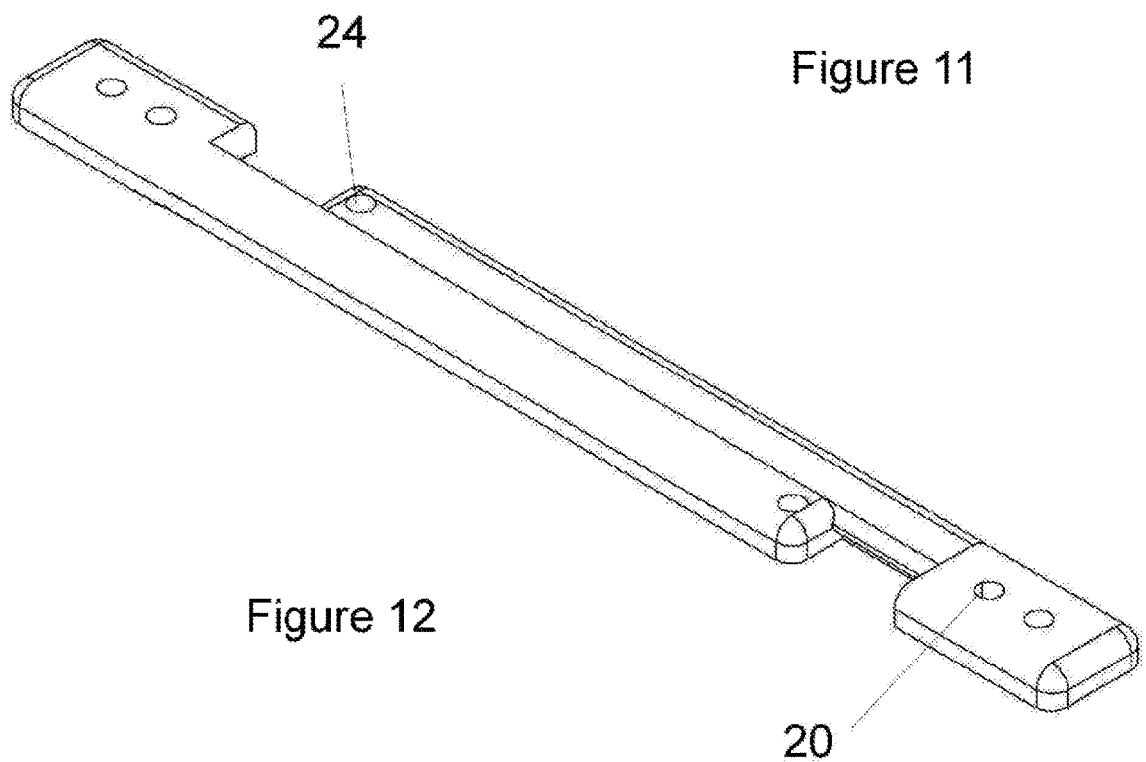
FIG. 12 is a perspective view of the device of FIG. 11.

The embodiment depicted in FIGS. 9 and 10 shows a relatively flattened device 10 wherein both the bone fixation regions 17a and 17b and the elongate mating surfaces 18a and 18b have in general a more planar structure. In cross section, as shown in FIG. 10b, this embodiment has a more rectangular cross section with rounded edges to avoid any damage to surrounding tissue.

In the embodiment depicted in FIGS. 9 and 10, the second ends 13 and 16 of the elongate members each comprise an aperture 24. Once a bone has been fully distracted or has achieved its full growth, a pin or screw may be inserted through said apertures 24 to fix the device to the bone and prevent any further movement of the elongate members 11, 14 relative to one another.

The device 10 of this embodiment may be connected to an external surface of a bone if intramedullary insertion is not feasible. In this example, flattened ends 13 and 16 can incorporate bone screws, either standard or locking screws. For larger bones, additional holes can be added in the flattened ends 13 and 16.

To achieve elongation of the device as the bone grows or is distracted by another method, it is necessary to secure the bone fixation regions 17a and 17b of the elongate members in the surrounding bone of a subject.

Figure 7A:
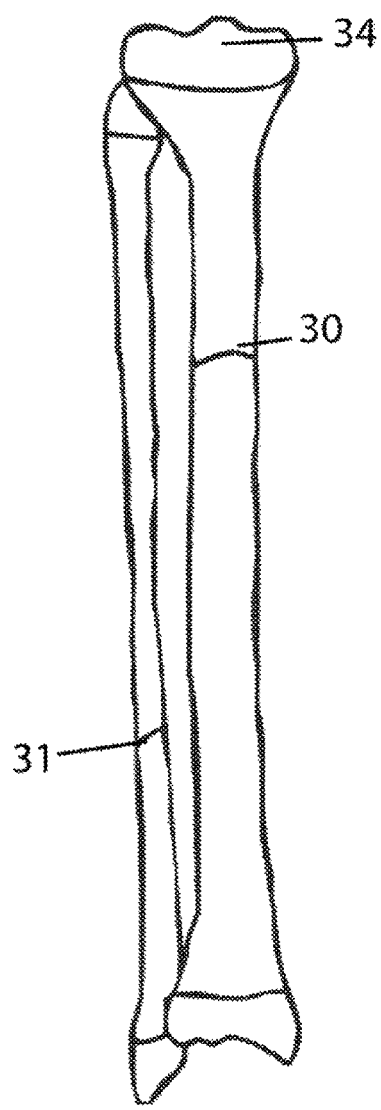
FIGS. 7a to 7c depict the steps in the process of using the device of the present disclosure in a fracture repair in a child.
Figure 7B:
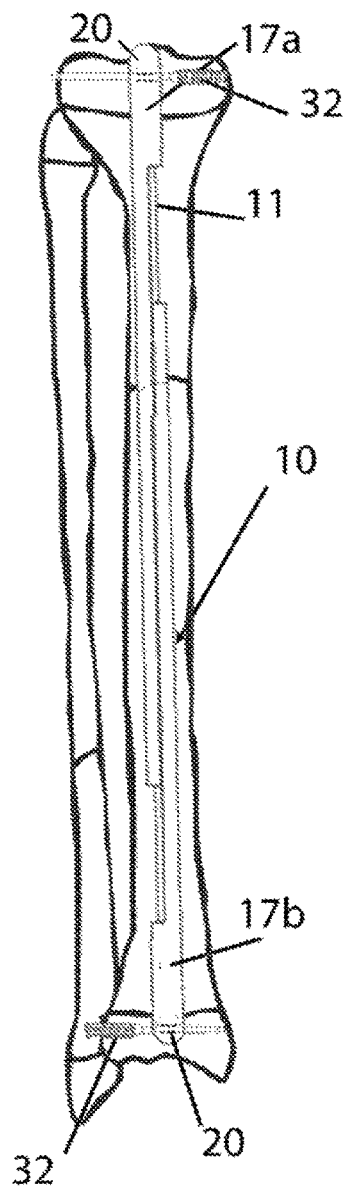
Figure 7C:

FIGS. 7a to 7c depict the steps of stabilising a fractured bone of a subject with the device 10 such that the device will continue to extend with the bone as the subject grows. FIG. 7a depicts a fracture of the tibia 30 and a fracture of the fibula 31.

Device 10 of the present disclosure is introduced through the medullary canal of the tibia until the bone fixation regions 17a and 17b of the elongate members are positioned correctly in the epiphyses 34. Once correctly positioned, the bone fixation regions 17a and 17b are secured to the surrounding bone. This may be achieved in a number of ways but as shown in FIG. 7b, each bone fixation region 17a and 17b is locked in place with a screw threaded nail 32 which is inserted through hole 20 in the epiphyses of the bone. FIG. 7c shows the device 10 after the fracture has healed, where the device 10 has extended with growth of the tibia.

Figure 8A:
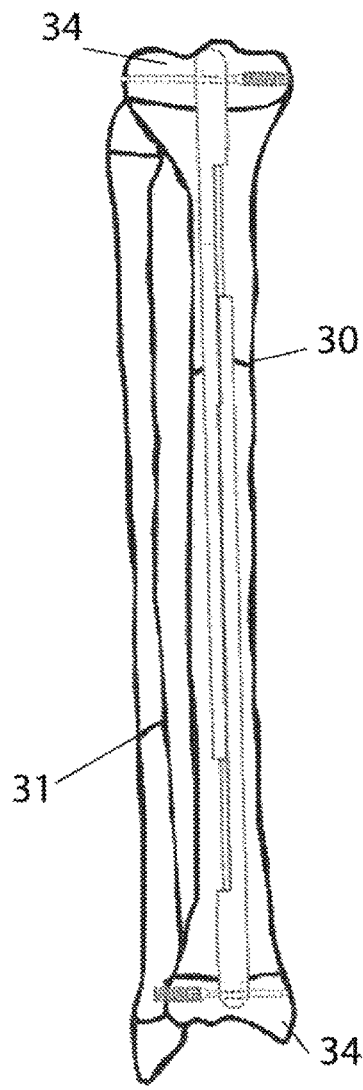
FIGS. 8a to 8c show use of the device of the present disclosure in a leg lengthening procedure.
Figure 8B:
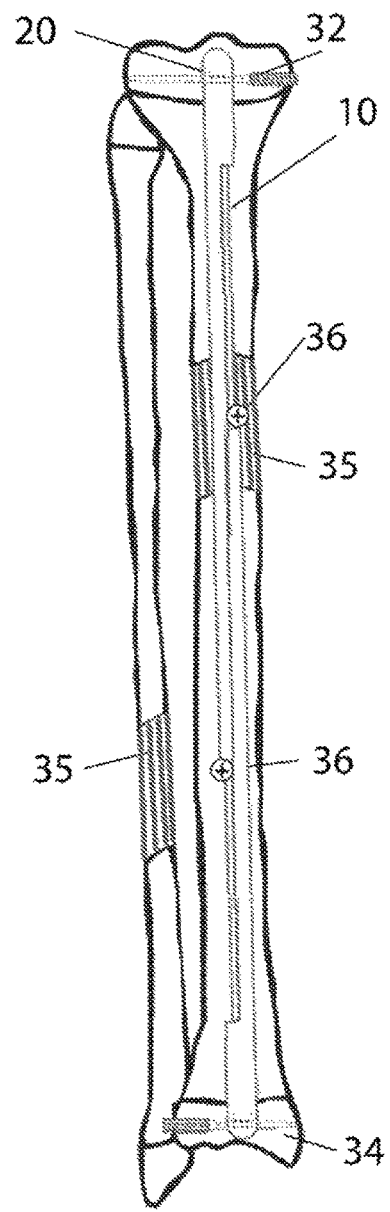
Figure 8C:
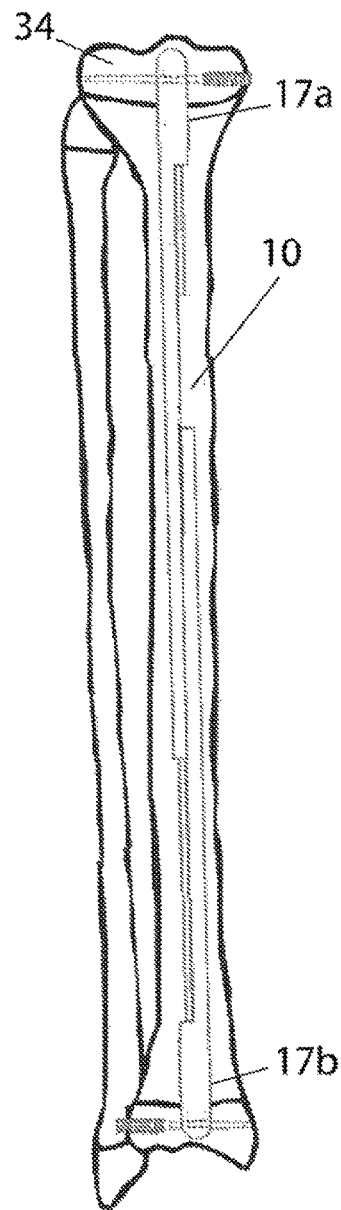

In FIGS. 8a to 8c, device 10 is used in a procedure of tibial lengthening. In this procedure the device is inserted into a tibia after corticotomy of tibia and fibula 30 and 31 respectively. As above, the bone fixation regions 17a and 17b are fixed in place in the epiphysis 34. Lengthening of the tibia is performed using an external lengthening device (not shown). At the end of a lengthening procedure, locking screws 36 are inserted to prevent shortening of the elongate members relative to each other. FIG. 8c depicts the healed bone and new bone growth 35, with the device 10 in an extended configuration.

Figure 13:
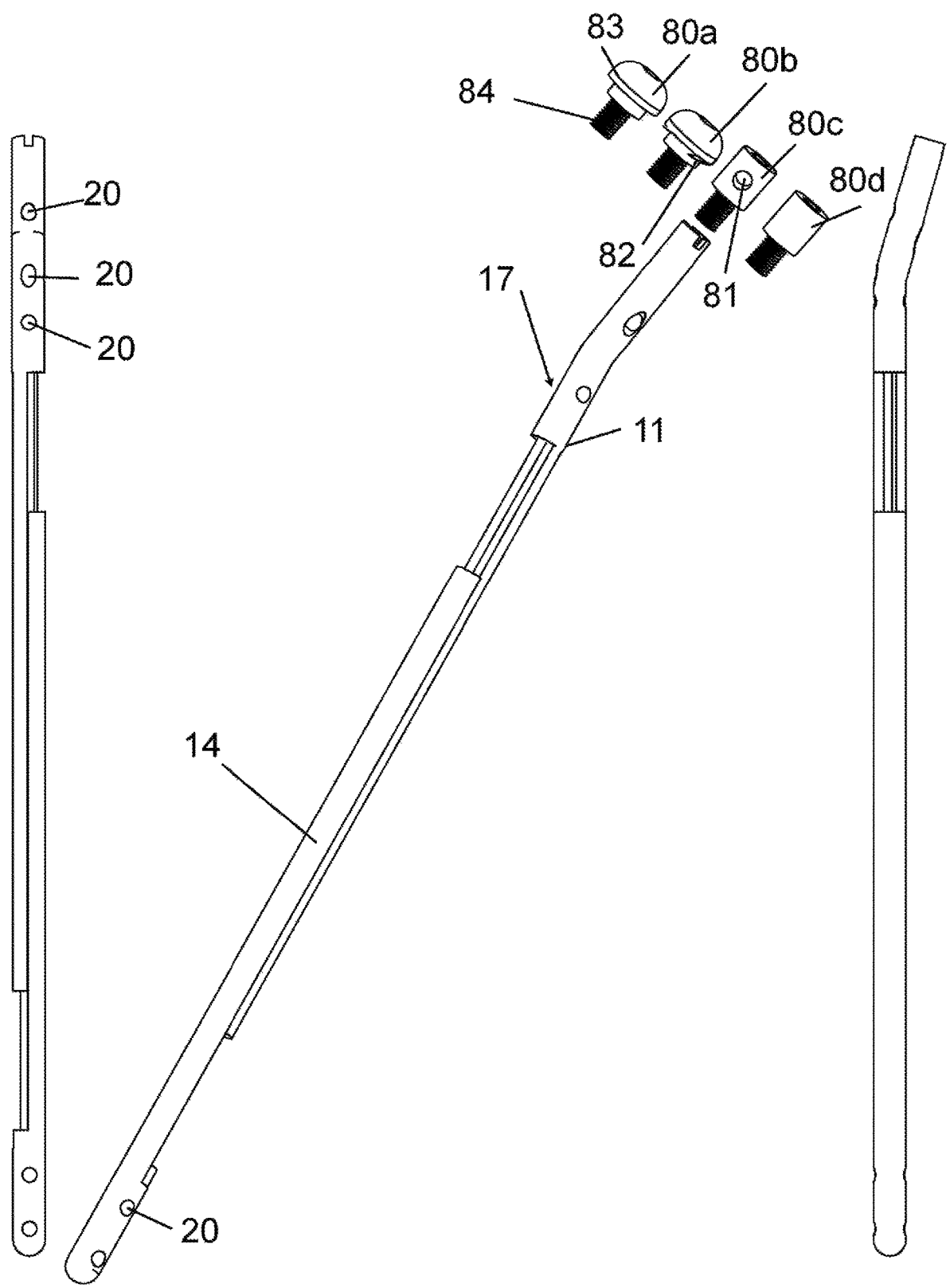
FIG. 13 shows different views of a further embodiment of the device of the present disclosure.

FIG. 13 depicts a modified device having an angled bone fixation region 17. For conventional telescopic rods it is very difficult to incorporate a Herzog bend for trochanteric entry. The angled region 17 of device 20 allows for trochanteric entry with proximal locking either into the trochanter, femoral neck or femoral shaft feasible. It is envisaged that such an angled region 17 would also be useful in the entry to other bones and not only the femur.

In any of the embodiments, either end 12 and 15 of the elongate members 11 and 14 may be closed or may be open to receive an end cap. Examples of suitable end caps are shown as 80a, 80b, 80c and 80d in FIG. 13. Each cap includes a head 83 and a threaded shaft 84. Shaft 84 is configured to be received into a complementary screw thread on the interior surface of bone fixation region 17a. The heads 83 may be substantially rounded as shown in 80a and 80b. Alternatively, the head may be substantially cylindrical. Other modifications include serrated teeth 82 on part of the head 83 to cut into the surrounding bone. In cap 80c, the head 83 includes an aperture 81 therethrough to receive a locking device such as a pin, screw, nail or K-wire.

Device 10 may be used in spinal procedures such as shown in FIGS. 14, 15 and 25a to 25d. The device depicted in FIG. 14b may also be used in spinal correction surgery but in that case, it is used in a more conventional system wherein the two elongate members 11 and 14 are moved relative to each other by an external motor and locked in place by clamp 92. That is, the driver for longitudinal extension of the elongate members 11 and 14 relative to one another is not the natural growth of the bone.

Figures 15A, 15B:
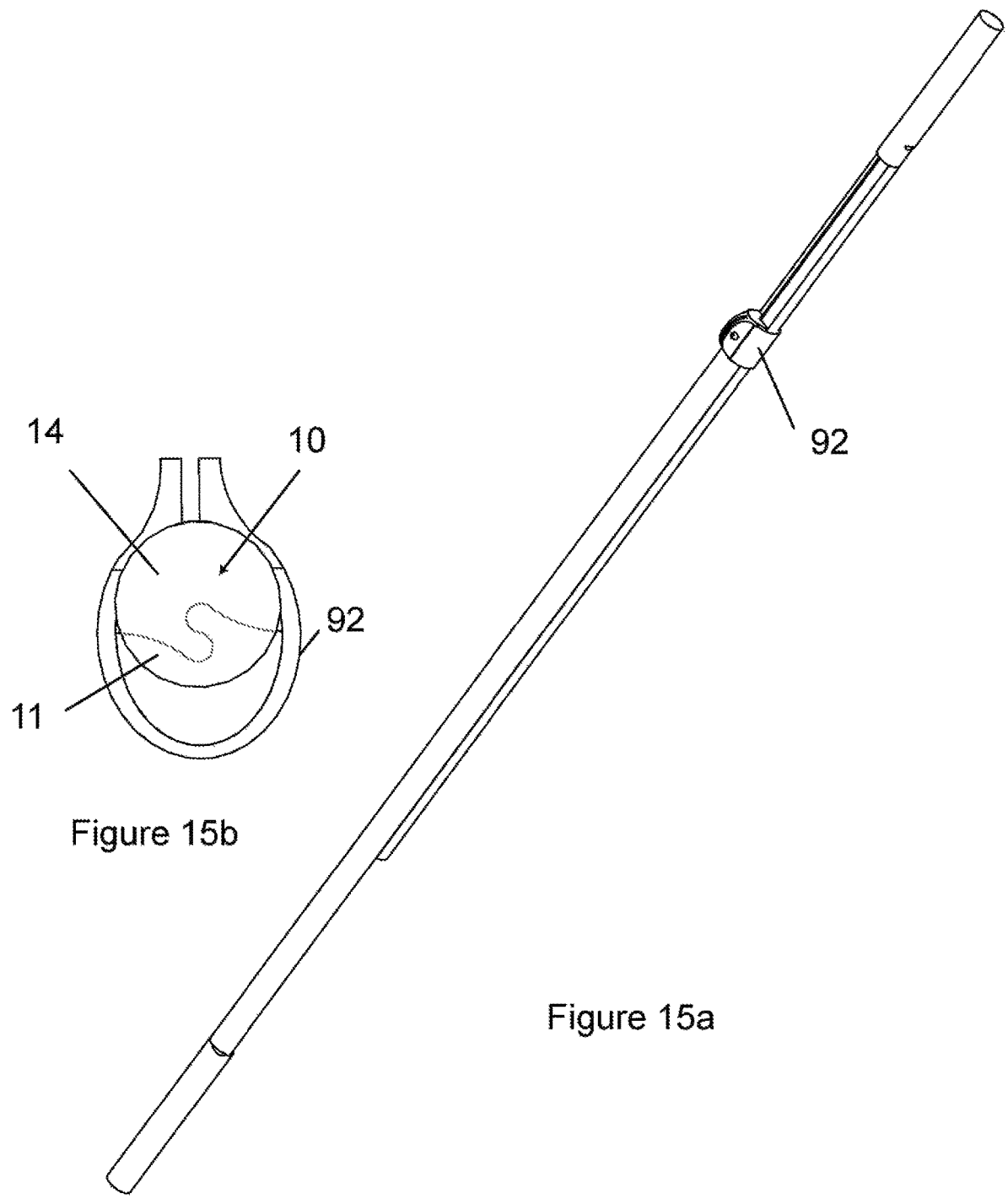
Figure 16:
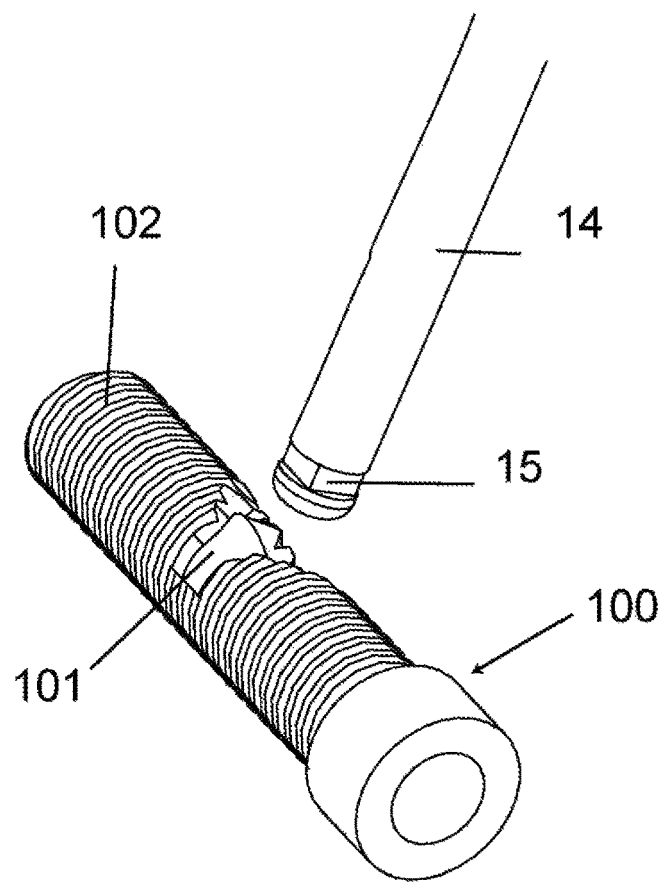
FIGS. 16 and 17 show a modified end of the device for use with a cross screw.

Another embodiment of the device for use in the growing spine is shown in FIGS. 15a and 15b. Here the elongate members have an oval or elliptic cross section when interdigitated, but the bone fixation regions 17a and 17b are cylindrical in cross section for fixation. The device 10 of this embodiment can be locked at any point of extension by clamp 92 and secured to the spine via the use of pedicle screws, sublaminar hooks or wires.

In contrast, in FIGS. 25b, 25c and 25d, a system of devices 10 is depicted for use in stabilisation of a spine of child as the child grows. Fixed rods 94 are used to provide anchor points along the spine of a patient. The devices 10 of the present disclosure may be attached therebetween to longitudinally extend as the child's spine grows. As shown, a central region of fixed rods 94 are fixed to fused vertebrae to correct the apex of the deformity. This is a non-lengthening section. A proximal fixed rod 94 is secured to the upper thoracic region and a distal rod 94 is fixed to the lower lumbar spine. The fixed rods 94 may be re-shaped to fit the sagittal curvature as desired and are held in place by pedicle screws 91. Fixation can also be achieved by but not limited to sublaminar hooks or wires, or by attachment to the ribs (not shown).

The device 10 is positioned between the fixed rods 94 to form a lengthening component of the assembly. In the embodiment depicted, the majority of the length of the device has an oval or elliptical cross section.

Figure 26C:
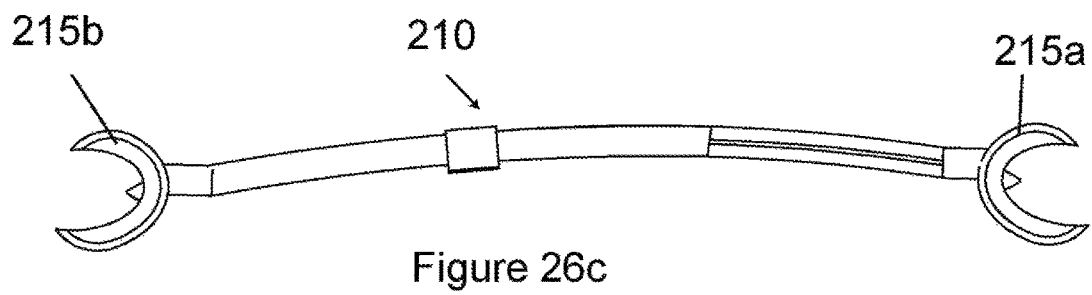
Figure 26A:
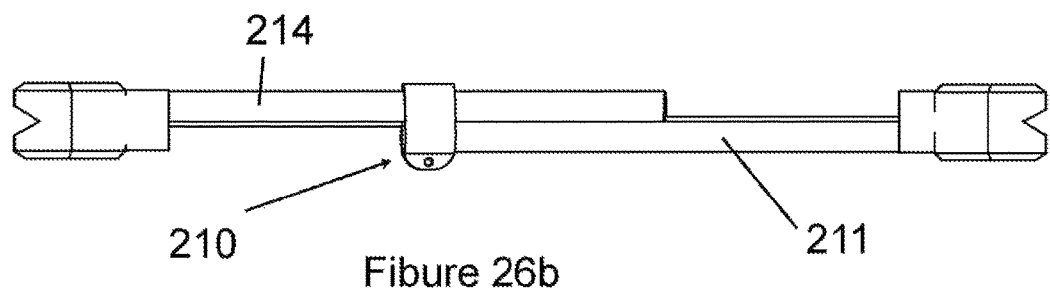
Figure 26A:
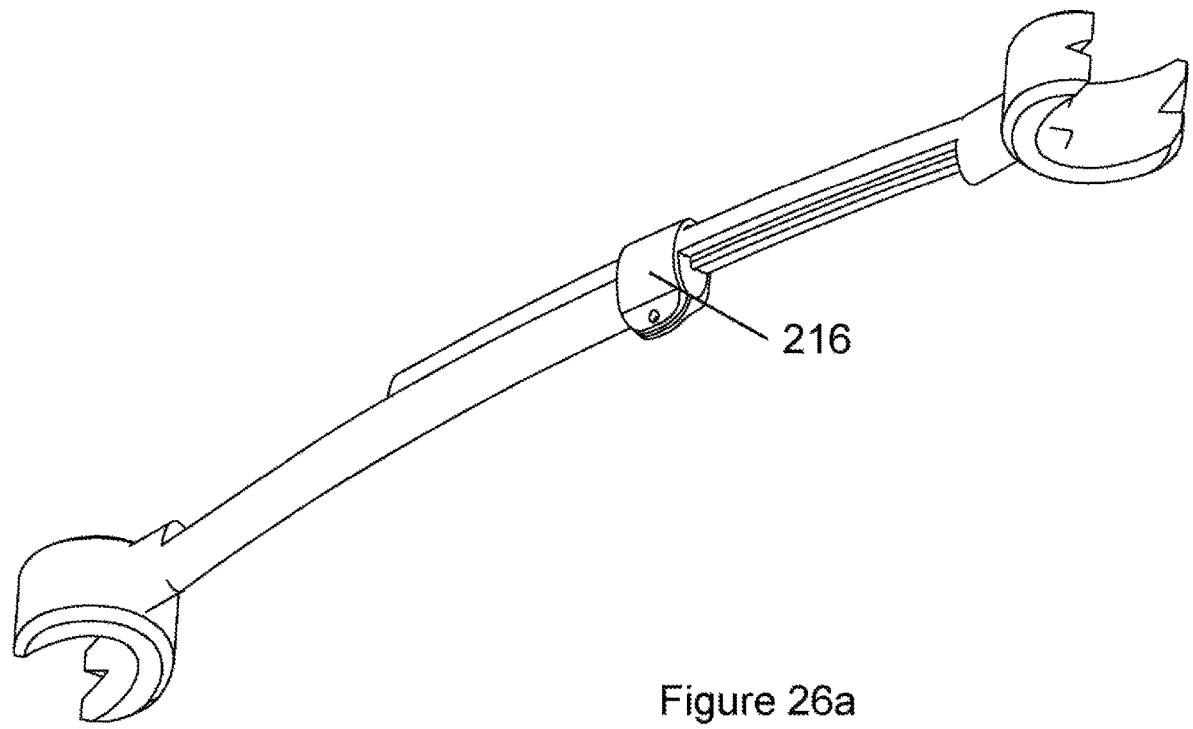

The embodiment of device 10 which is depicted in FIGS. 26a, 26b and 26c is adapted for use in ribs. In this embodiment, the device 210 includes a first elongate member 211 and a second elongate member 214 which may be longitudinally extended as discussed above in relation to the other embodiments. Bone fixation regions 215a and 215b form curved C-shaped structures adapted to at least partially surround a rib of a subject. Once the device 210 is in a desirable extension between two adjacent ribs, the elongate members 211 and 214 may be locked in place relative to one another by clamp 216.

It will be appreciated by persons skilled in the art that numerous variations and/or modifications may be made to the above-described embodiments, without departing from the broad general scope of the present disclosure. The present embodiments are, therefore, to be considered in all respects as illustrative and not restrictive.

The invention claimed is:

1. An intramedullary orthopaedic device comprising:
an intramedullary rod configured for insertion into a bone; said intramedullary rod including:
a first elongate member extending from a first end to a second end and including a first bone fixation region adjacent the first end and a first mating surface; and
a second elongate member extending from a first end to a second end and including a second bone fixation region adjacent the first end and a second mating surface;
wherein the first mating surface and the second mating surface are each adapted and configured to engage with each other to form a mating region and wherein at the mating region the intramedullary rod is a non-tubular structure and after insertion into a bone the engagement of the first surface with the second surface is such that the elongate members are longitudinally moveable but not rotationally moveable relative to each other;
wherein the first mating surface comprises a first elongate ridge and a first elongate groove, and the first elongate groove has a shape that is the inverse of the shape of the first elongate ridge.

2. The intramedullary orthopaedic device according to claim 1, wherein the first elongate ridge extends from a base of the mating surface and has a variable diameter along its extension.

3. The intramedullary orthopaedic device of claim 2, wherein the first elongate ridge comprises a relatively narrow neck extending into a relatively wider protrusion.

4. The intramedullary orthopaedic device according to claim 1, wherein at least part of the first elongate ridge defines part of an opening of the first elongate groove.

5. The intramedullary orthopaedic device according to claim 4, wherein the first elongate groove has a wider base relative to the opening.

6. The intramedullary orthopaedic device according to claim 1 wherein the second mating surface comprises a second elongate ridge and a second elongate groove.

7. The intramedullary orthopaedic device according to claim 6, wherein the second elongate ridge extends from a base of the second mating surface and has a variable diameter along its extension.

8. The intramedullary orthopaedic device of claim 7, wherein the second elongate ridge comprises a relatively narrow neck extending into a relatively wider protrusion.

9. The intramedullary orthopaedic device according to claim 6, wherein at least part of the second elongate groove is defined by at least part of the second elongate ridge.

10. The intramedullary orthopaedic device according to claim 6, wherein at least part of the second elongate ridge defines part of an opening of the second elongate groove.

11. The intramedullary orthopaedic device according to claim 10, wherein the second elongate groove has a wider base relative to the opening.

12. The intramedullary orthopaedic device according to claim 6, wherein the second elongate groove is a shape that is the inverse of the shape of the second elongate ridge.

13. The intramedullary orthopaedic device according to claim 1, wherein the first elongate member further comprises a first non-mating surface and the second elongate member comprises a second non-mating surface.

14. The intramedullary orthopaedic device according to claim 13, wherein the first non-mating surface is substantially identical to the second non-mating surface.

15. The intramedullary orthopaedic device according to claim 14, wherein when the first mating surface is in engagement with the second mating surface, the first non-mating surface and the second non-mating surface together define an outer surface of the intramedullary orthopaedic device.

16. The intramedullary orthopaedic device according to claim 15, wherein the outer surface is substantially circular in cross section.

17. The intramedullary orthopaedic device according to claim 1, wherein the first bone fixation region includes an aperture in the first elongate member.

18. The intramedullary orthopaedic device according to claim 17, wherein said aperture is configured to receive a locking member.

19. The intramedullary orthopaedic device of claim 1, wherein the first mating surface and the second mating surface are configured for interdigitating engagement with each other.

20. The intramedullary orthopaedic device of claim 1, which further comprises a threaded end cap on the first bone fixation region.

21. The intramedullary orthopaedic device of claim 20, wherein said end cap includes an aperture therethrough to receive a bone locking device.

22. The intramedullary orthopaedic device of claim 20, wherein said end cap has a substantially rounded head.

23. An intramedullary orthopaedic device comprising:
an intramedullary rod configured for insertion into a bone; said intramedullary rod including:
a first elongate member extending from a first end to a second end and including a first bone fixation region adjacent the first end and a first mating surface; and
a second elongate member extending from a first end to a second end and including a second bone fixation region adjacent the first end and a second mating surface;
wherein the first mating surface and the second mating surface are each adapted and configured to engage with each other to form a mating region and wherein at the mating region the intramedullary rod is a non-tubular structure and after insertion into a bone the engagement of the first surface with the second surface is such that the elongate members are longitudinally moveable but not rotationally moveable relative to each other;
wherein the second mating surface comprises a second elongate ridge and a second elongate groove; wherein the second elongate ridge has a variable diameter along its extension;
wherein the second elongate ridge comprises a relatively narrow neck extending into a relatively wider protrusion.

24. The intramedullary orthopaedic device according to claim 23, wherein the first mating surface comprises a first elongate ridge and a first elongate groove.

25. The intramedullary orthopaedic device according to claim 24, wherein the first elongate ridge extends from a base of the mating surface and has a variable diameter along its extension.

26. The intramedullary orthopaedic device of claim 24, wherein the first elongate ridge comprises a relatively narrow neck extending into a relatively wider protrusion.

27. The intramedullary orthopaedic device according to claim 24, wherein the first elongate groove has a wider base relative to the opening.

28. The intramedullary orthopaedic device according to claim 23, wherein the second elongate groove is a shape that is the inverse of the shape of the second elongate ridge.

29. The intramedullary orthopaedic device according to claim 23, wherein the first bone fixation region includes an aperture in the first elongate member configured to receive a locking member.

30. The intramedullary orthopaedic device of claim 23, wherein the first mating surface and the second mating surface are configured for interdigitating engagement with each other.

31. The intramedullary orthopaedic device of claim 23, which further comprises a threaded end cap on the first bone fixation region, wherein said end cap includes an aperture therethrough to receive a bone locking device.

32. The intramedullary orthopaedic device of claim 31, wherein said end cap has a substantially rounded head.

33. The intramedullary orthopaedic device of claim 23, wherein the second elongate ridge extends from a base of the second mating surface.

34. An intramedullary orthopaedic device comprising:
an intramedullary rod configured for insertion into a bone; said intramedullary rod including:
a first elongate member extending from a first end to a second end and including a first bone fixation region adjacent the first end and a first mating surface; and
a second elongate member extending from a first end to a second end and including a second bone fixation region adjacent the first end and a second mating surface;
wherein the first mating surface and the second mating surface are each adapted and configured to engage with each other to form a mating region and wherein at the mating region the intramedullary rod is a non-tubular structure and after insertion into a bone the engagement of the first surface with the second surface is such that the elongate members are longitudinally moveable but not rotationally moveable relative to each other;
wherein the second mating surface comprises a second elongate ridge and a second elongate groove, at least part of the second elongate groove is defined by at least part of the second elongate ridge, at least part of the second elongate ridge defines part of an opening of the second elongate groove, and the second elongate groove has a wider base relative to the opening.

35. The intramedullary orthopaedic device according to claim 34, wherein the first mating surface comprises a first elongate ridge and a first elongate groove, wherein the first elongate ridge extends from a base of the mating surface and has a variable diameter along its extension.

36. The intramedullary orthopaedic device of claim 35, wherein the first elongate ridge comprises a relatively narrow neck extending into a relatively wider protrusion.

37. The intramedullary orthopaedic device according to claim 35, wherein the first elongate groove has a wider base relative to the opening.

38. The intramedullary orthopaedic device according to claim 35, wherein the second elongate ridge extends from a base of the second mating surface and has a variable diameter along its extension.

39. The intramedullary orthopaedic device according to claim 35, wherein the second elongate groove is a shape that is the inverse of the shape of the second elongate ridge.

40. The intramedullary orthopaedic device according to claim 34, wherein the first bone fixation region includes an aperture in the first elongate member.

41. The intramedullary orthopaedic device according to claim 40, wherein said aperture is configured to receive a locking member.

42. The intramedullary orthopaedic device of claim 34, wherein the first mating surface and the second mating surface are configured for interdigitating engagement with each other.

43. The intramedullary orthopaedic device of claim 34, which further comprises a threaded end cap on the first bone fixation region.

44. An intramedullary orthopaedic device comprising:
an intramedullary rod configured for insertion into a bone; said intramedullary rod including:
a first elongate member extending between opposing first and second ends and including a first bone fixation region adjacent the first end and a first mating surface extending from the second end;
a threaded end cap on the first end of said first elongate member; and
a second elongate member extending between opposing first and second ends and including a second bone fixation region adjacent the first end and a second mating surface extending from the second end;
wherein the first mating surface and the second mating surface are each adapted and configured to engage with each other by bringing the second end of said first elongate member into engagement with the second end of said second elongate member to form a mating region and wherein at the mating region the intramedullary rod is a non-tubular structure and after insertion into a bone the engagement of the first surface with the second surface is such that the elongate members are longitudinally moveable but not rotationally moveable relative to each other.

45. The intramedullary orthopaedic device according to claim 44, wherein the first mating surface comprises a first elongate ridge and a first elongate groove, wherein the first elongate ridge extends from a base of the mating surface and has a variable diameter along its extension.

46. The intramedullary orthopaedic device of claim 45, wherein the first elongate ridge comprises a relatively narrow neck extending into a relatively wider protrusion.

47. The intramedullary orthopaedic device according to claim 44, wherein the second bone fixation region includes an aperture in the second elongate member.

48. The intramedullary orthopaedic device according to claim 47, wherein said aperture is configured to receive a locking member.

49. The intramedullary orthopaedic device of claim 44, wherein the first mating surface and the second mating surface are configured for interdigitating engagement with each other.

50. The intramedullary orthopaedic device of claim 44 wherein said end cap includes an aperture therethrough to receive a bone locking device.

51. The intramedullary orthopaedic device of claim 44 wherein after engagement the first end of said first elongate member is opposite to the first end of said second elongate member.

52. The intramedullary orthopaedic device of claim 44 wherein said end cap has a substantially rounded head.

* * * * *